US009181237B2

(12) United States Patent
Grote

(10) Patent No.: US 9,181,237 B2
(45) Date of Patent: Nov. 10, 2015

(54) SUBSTITUTED BERBINES AND THEIR SYNTHESIS

(71) Applicant: MALLINCKRODT LLC, Hazelwood, MO (US)

(72) Inventor: Christopher W. Grote, Webster Groves, MO (US)

(73) Assignee: Mallinckrodt LLC, Hazelwood, MI (US)

( * ) Notice: Subject to any disclaimer, the term of this patent is extended or adjusted under 35 U.S.C. 154(b) by 0 days.

(21) Appl. No.: 14/504,906

(22) Filed: Oct. 2, 2014

(65) Prior Publication Data

US 2015/0099772 A1    Apr. 9, 2015

Related U.S. Application Data

(60) Provisional application No. 61/886,695, filed on Oct. 4, 2013.

(51) Int. Cl.
*C07D 221/18* (2006.01)
*C07D 221/04* (2006.01)
*C07D 455/03* (2006.01)

(52) U.S. Cl.
CPC .................................. *C07D 455/03* (2013.01)

(58) Field of Classification Search
USPC ...................................................... 546/73, 71
See application file for complete search history.

(56) References Cited

U.S. PATENT DOCUMENTS

| | | | | |
|---|---|---|---|---|
| 4,013,666 | A * | 3/1977 | Lenz | 546/71 |
| 4,052,389 | A | 10/1977 | Monkovic | |
| 6,255,317 | B1 | 7/2001 | Kim | |
| 8,003,795 | B2 | 8/2011 | Liu | |
| 8,163,912 | B2 | 4/2012 | Grote | |
| 8,431,705 | B2 | 4/2013 | Grote | |
| 2010/0113494 | A1 | 5/2010 | Hu | |
| 2010/0120810 | A1* | 5/2010 | Leblond et al. | 514/280 |
| 2012/0004223 | A1 | 1/2012 | Liu | |
| 2012/0059026 | A1 | 3/2012 | LaVoie | |

FOREIGN PATENT DOCUMENTS

| | | |
|---|---|---|
| EP | 0 028 959 | 5/1981 |
| WO | 2009/007457 | 1/2009 |
| WO | 2010/075469 | 7/2010 |
| WO | 2010/128061 | 11/2010 |
| WO | 2012/163179 | 12/2012 |

OTHER PUBLICATIONS

Jiaranaikulwanitch, J. et al.: Triazolyl tryptoline derivatives as beta-secretase inhibitors. Biorg. & medicinal Chem. letters, vol. 20, pp. 6572-6576, 2010.*
Kobayashi, J. et al.: Theoneberine; The first brominated benzyltetrahydroberberine alkaloid from the Okinawan marine sponge *Theonella* sp., vol. 57, pp. 6680-6682, 1992.*
Rastrelli, L. et al.: New Protopine and benzyltetrahydroprotoberberine alkaloids from *Aristolochia constricta* and their activity on isolated guinea-pig ileum. J. of Natural Prod., vol. 60, pp. 1065-1069, 1997.*
Grycova et al., Quaternary protoberberine alkaloids, Phytochem. 2007, 68(2): 150-175.
Mali et al., Novel syntheses of 1-substituted-7,8-dialkoxyisochroman-3-ones and 8-substituted-2,3,9,10-tetramethoxyberbines, Tetrahedron (1986), 42(7), 2075-82.
Memetzidis, et al., Synthesis of Aromatic Chloroberbines, Heterocycles (1990), 31(2), 341-51.
Memetzidis, et al., Structure-affinity relationships of berbines or 5,6,13,13a-tetrahydro-8H-dibenzo[a,g]quinolizines at α-adrenoceptors, Eur. J. Med. Chem., 1991, 26: 605-611.
Nagubandi et al., The mechanism of the Bischler-Napierski reaction, J. Heterocyclic Chem., 1980, 17: 1457-1463.
Sotomayor et al., Bischler-Napieralski Cyclization-N/C-Alkylation Sequences for the Construction of Isoquinoline Alkaloids. Synthesis of Protoberberines and Benzo[c]phenanthridines via C-2'-Functionalized 3-Arylisoquinolines, Journal of Organic Chemistry (1996), 61(12), 4062-4072.
Valpuesta et al., Regio-and Stereoselective Stevens Rearrangement of Benzyltetrahydroprotoberberinium Salts, Eur. J. Org. Chem. 2004, 4313-4318.
Yamamoto et al., Total synthesis of 8-epi-javaberine A and javaberine A, Heterocycles 2014, 88(2): 1311-1321.
Zhang, et al., A Novel Analgesic Isolated from a Traditional Chinese Medicine, Current Biology, 2014, vol. 24 (2), pp. 1-7.
International Search Report and Written Opinion dated Jan. 14, 2015 from related international application No. PCT/US2014/058806, 11 pgs.
PubChem, Compound Summary for CID 6342, Acetonitrile, Create Date: Sep. 16, 2004. [retrieved on 20.22.2014 from the Internet] pubchem.ncbi.nlm.nih.gov/6342.
PubChem, Compound Summary for CID 8025, Ethyl formate, Create Date: Mar. 26, 2005. [retrieved on Nov. 21, 2014 from the Internet] pubchem.ncbi.nlm.nih.gov/8025.

* cited by examiner

*Primary Examiner* — Charanjit Aulakh

(57) ABSTRACT

The present invention provides substituted berbines, processes for the synthesis of substituted berbine compounds, as well as intermediates used in the synthesis of substituted berbine compounds. Also provided are methods for using the substituted berbines to inhibit cancer cell growth.

5 Claims, No Drawings

SUBSTITUTED BERBINES AND THEIR SYNTHESIS

CROSS-REFERENCE TO RELATED APPLICATIONS

This application claims the priority of U.S. provisional application Ser. No. 61/886,696, filed Oct. 4, 2013, which is hereby incorporated by reference in its entirety.

FIELD OF THE INVENTION

The present invention generally relates to substituted berbines, processes for the synthesis of substituted berbines, intermediate compounds used in the preparation of substituted berbines, and methods of using substituted berbines.

BACKGROUND OF THE INVENTION

The berbine class of heterocyclic compounds is structurally related to the plant alkaloid berberine. Berbine compounds have been reported to have numerous therapeutic effects. For example, they have been found to have antibacterial, antifungal, antiparasitic, antipyretic, antihypertensive, antidepressant, antiemetic, tranquilizing, and analgesic activities. Because of the potential therapeutic value of berbine compounds and derivatives thereof, there is a need for new derivatives than may be more potent and/or efficacious. Moreover, there is a need for efficient synthesis processes for the preparation of pure preparations of specific enantiomers of these substituted berbines.

SUMMARY OF THE INVENTION

Among the various aspects of the present invention is a compound comprising Formula (V-1):

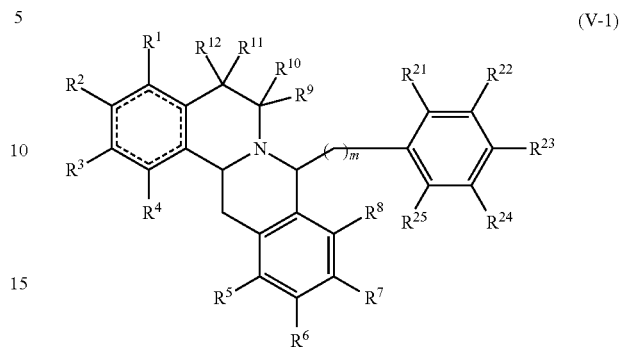

(V-1)

wherein:
  $R^1$ $R^2$, $R^3$, and $R^4$ independently are hydrogen, halogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising $\{-\}O(CH_2)_nO\{-\}$;
  $R^5$, $R^6$, $R^7$, and $R^8$ independently are hydrogen, halogen, $OR^{15}$, $NR^{15}N^{16}$, nitro, cyano, thiol, hydrocarbyl, substituted hydrocarbyl, or together $R^6$ and $R^7$ along with the ring carbons to which they are attached form a ring comprising $\{-\}O(CH_2)_nO\{-\}$; provided that at least two of $R^6$, $R^7$, and $R^8$ are other than methoxy;
  $R^9$, $R^{10}$, $R^{11}$, and $R^{12}$ independently are hydrogen, hydrocarbyl, or substituted hydrocarbyl;
  $R^{21}$, $R^{22}$, $R^{23}$, $R^{24}$, and $R^{25}$ independently are hydrogen, halogen, $OR^{15}$, $NR^{15}N^{16}$, nitro, cyano, thiol, hydrocarbyl, or substituted hydrocarbyl;
  $R^{15}$ and $R^{16}$ independently are hydrogen, hydrocarbyl, or substituted hydrocarbyl;
  m is an integer of 0 or greater;
  n is an integer from 1 to 3; and
  the dashed lines represent optional double bonds.

Another aspect of the disclosure encompasses a process for preparing a compound comprising Formula (V). The process comprises contacting a compound comprising Formula (II) with a cyclizing agent to form a compound comprising Formula (IV), and contacting the compound comprising Formula (IV) with a reducing agent to form the compound comprising Formula (V) according to the following reaction scheme:

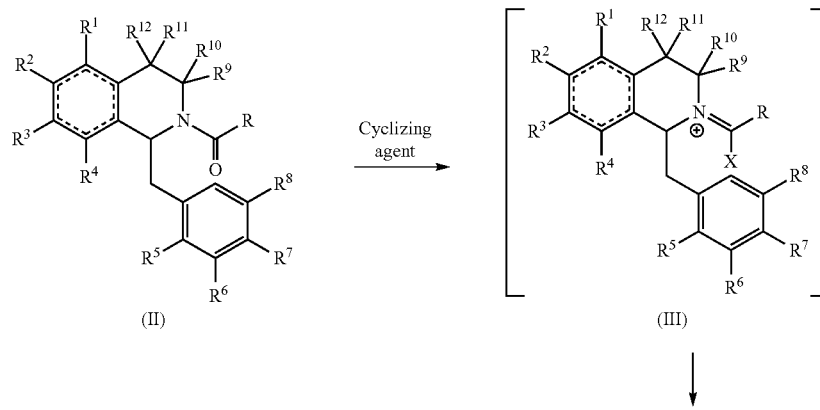

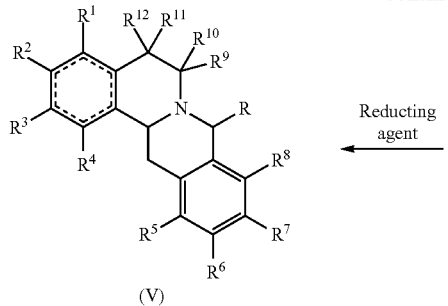

(V)

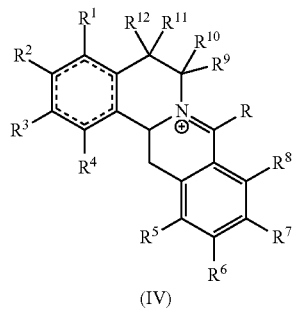

(IV)

wherein:
R is hydrogen, hydrocarbyl, or substituted hydrocarbyl;
$R^1$ $R^2$, $R^3$, and $R^4$ independently are hydrogen, halogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising {—}$O(CH_2)_nO${—};
$R^5$, $R^6$, $R^7$, and $R^8$ independently are hydrogen, halogen, $OR^{15}$, $NR^{15}N$ nitro, cyano, thiol, hydrocarbyl, substituted hydrocarbyl, or together $R^6$ and $R^7$ along with the ring carbons to which they are attached form a ring comprising {—}$O(CH_2)_nO${—};
$R^9$, $R^{10}$, $R^{11}$, $R^{12}$, $R^{15}$, and $R^{16}$ independently are hydrogen, hydrocarbyl, or substituted hydrocarbyl;
n is an integer from 1 to 3;
X is halogen, {—}$OSO_2R^{18}$, or {—}$OCOR^{18}$, wherein $R^{18}$ is hydrocarbyl or substituted hydrocarbyl; and
the dashed lines represent optional double bonds.

A further aspect of the present disclosure provides a method for inhibiting growth of a cancer cell. The method comprises contacting the cancer cell with an effective amount of a compound comprising Formula (V):

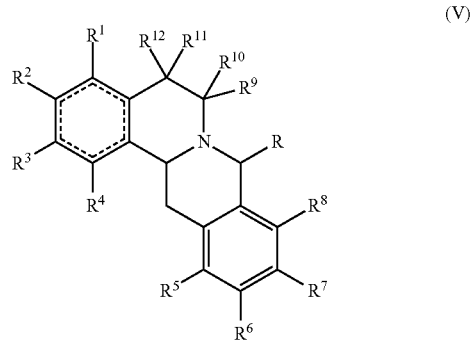

wherein:
R is hydrogen, hydrocarbyl, or substituted hydrocarbyl;
$R^1$ $R^2$, $R^3$, and $R^4$ independently are hydrogen, halogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising {—}$O(CH_2)_nO${—};
$R^5$, $R^6$, $R^7$, and $R^8$ independently are hydrogen, halogen, $OR^{15}$, $NR^{15}N$ nitro, cyano, thiol, hydrocarbyl, substituted hydrocarbyl, or together $R^6$ and $R^7$ along with the ring carbons to which they are attached form a ring comprising {—}$O(CH_2)_nO${—};
$R^9$, $R^{10}$, $R^{11}$, $R^{12}$, $R^{15}$, and $R^{16}$ independently are hydrogen, hydrocarbyl, or substituted hydrocarbyl;
n is an integer from 1 to 3; and
the dashed lines represent optional double bonds.

Other aspects and features of the invention will be in part apparent and in part pointed out hereinafter.

DETAILED DESCRIPTION

The present invention provides new substituted berbine compounds and processes for preparing substituted berbines, as well as intermediate compounds for use in the preparation of substituted berbines. The processes disclosed herein allow for regiochemical and stereochemical synthesis of substituted berbines. For example, syn diastereomers may be prepared using the processes disclosed herein. Furthermore, the processes disclosed herein are more efficient, more specific, and provide greater yields than currently available synthesis processes. Additionally, it has been discovered that substituted berbine compounds inhibit cancer cell growth.

For ease of discussion, the ring atoms of berbine compounds are numbered as diagrammed below.

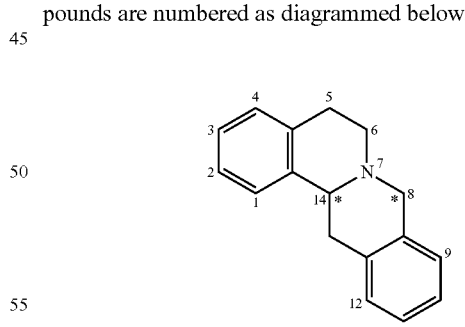

Substituted berbine compounds may have at least two chiral carbons, namely, C-14 and C-8, as indicated above with asterisks.

(I) Compounds (a) Compounds Comprising Formula (III)

One aspect of the present disclosure encompasses compounds that may be used as intermediates in the preparation of substituted berbine compounds. In general, the intermediate compounds comprise Formula (III):

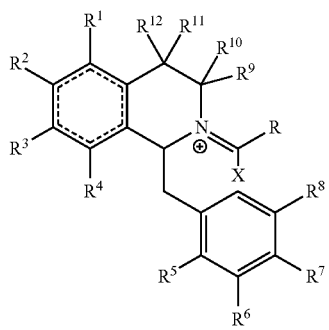

(III)

wherein:

R is hydrogen, hydrocarbyl, or substituted hydrocarbyl;

$R^1$, $R^2$, $R^3$, and $R^4$ independently are hydrogen, halogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising $\{-\}O(CH_2)_nO\{-\}$;

$R^5$, $R^6$, $R^7$, and $R^8$ independently are hydrogen, halogen, $OR^{15}$, $NR^{15}N$ nitro, cyano, thiol, hydrocarbyl, substituted hydrocarbyl, or together $R^6$ and $R^7$ along with the ring carbons to which they are attached form a ring comprising $\{-\}O(CH_2)_nO\{-\}$;

$R^9$, $R^{10}$, $R^{11}$, $R^{12}$, $R^{15}$, and $R^{16}$ independently are hydrogen, hydrocarbyl, or substituted hydrocarbyl;

n is an integer from 1 to 3;

X is halogen, $\{-\}OSO_2R^{18}$, or $\{-\}OCOR^{18}$, wherein $R^{18}$ is hydrocarbyl or substituted hydrocarbyl; and the dashed lines represent optional double bonds.

In some embodiments, R may be hydrogen, alkyl, heterocylic, aryl, heteroaryl, substituted alkyl, substituted heterocyclic, substituted aryl, or substituted heteroaryl. In various iterations, R may be lower alkyl, which is defined herein as $C_1$-$C_6$, and may be linear or cyclic. In other iterations, R may be morpholinyl, piperizinyl, phenyl, benzyl, pyridyl, pyridazinyl, pyranyl, oxazinyl, piperonyl, etc. Any of the foregoing may be substituted with at least one alkyl, alkenyl, alkynyl, aryl, halogen, oxo, keto, hydroxy, acyl, acyloxy, alkoxy, alkenoxy, alkynoxy, aryloxy, nitro, amino, amine, amide, thiol, cyano, ketal, acetal, ester, or ether.

In various embodiments $R^2$ and $R^3$ independently may be hydrogen, halogen, hydroxy, alkyoxy, alkyl or together $R^2$ and $R^3$ may form $\{-\}O-CH_2-O\{-\}$. In other embodiments, $R^5$ and $R^8$ independently may be hydrogen, halogen, hydroxy, alkoxy, or alkyl. In further embodiments, $R^6$ and $R^7$ independently may be hydrogen, halogen, hydroxy, alkoxy, alkyl, aryloxy, substituted aryloxy, nitro, amino, amine, or amide. In other embodiments, each of $R^9$, $R^{10}$, $R^{11}$, and $R^{12}$ may be hydrogen. In various embodiments, the ring containing the dashed lines may have one, two, or three double bonds. In certain embodiments, X may be chloride, bromide, $\{-\}OSO_2$-trifluoromethane, $\{-\}OSO_2$-methane, or $\{-\}OSO_2$-toluene. The configuration of C-14 may be R or S.

In specific embodiments, R may be heterocyclo, substituted heterocyclo, aryl, substituted aryl, heteroaryl, or substituted heteroaryl. In some embodiments, R may be phenyl, substituted phenyl, benzyl, or substituted benzyl. For example, the substituted phenyl or substituted benzyl may have at least one substituent chosen from halogen, hydroxy, alkoxy, alkyl, nitro, amino, or amine.

In one alternative of this embodiment, the compound comprising Formula (III) may be a compound comprising Formula (IIIa):

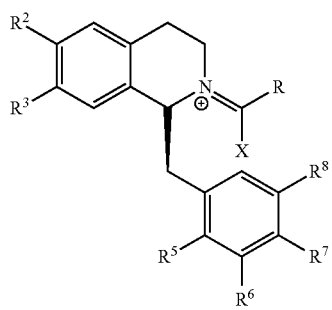

(IIIa)

wherein:

R is hydrogen, alkyl, substituted alkyl, heterocyclo, substituted heterocyclo, aryl, substituted aryl, heteroaryl, or substituted heteroaryl;

$R^2$ is hydroxy or alkyoxy and $R^3$ is hydrogen, or together $R^2$ and $R^3$ form $\{-\}O-CH_2-O\{-\}$ $R^5$ and $R^8$ independently are hydrogen, halogen, hydroxy, alkoxy, or alkyl;

$R^6$ and $R^7$ independently hydrogen, halogen, hydroxy, alkyoxy, alkyl aryloxy, substituted aryloxy, nitro, amino, amine, or amide; and X is halogen, $\{-\}OSO_2R^{18}$, or $\{-\}OCOR^{18}$, wherein $R^{18}$ is hydrocarbyl or substituted hydrocarbyl.

In another alternative of this embodiment, the compound comprising Formula (III) may be a compound comprising Formula (IIIb):

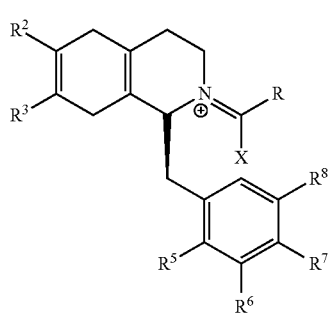

(IIIb)

wherein:

R is hydrogen, alkyl, substituted alkyl, heterocyclo, substituted heterocyclo, aryl, substituted aryl, heteroaryl, or substituted heteroaryl;

$R^2$ is hydroxy or alkyoxy and $R^3$ is hydrogen, or together $R^2$ and $R^3$ form $\{-\}O-CH_2-O\{-\}$ $R^5$ and $R^8$ independently are hydrogen, halogen, hydroxy, alkoxy, or alkyl;

$R^6$ and $R^7$ independently hydrogen, halogen, hydroxy, alkyoxy, alkyl aryloxy, substituted aryloxy, nitro, amino, amine, or amide; and X is halogen, $\{-\}OSO_2R^{18}$, or $\{-\}OCOR^{18}$, wherein $R^{18}$ is hydrocarbyl or substituted hydrocarbyl.

(b) Compounds Comprising Formula (IV)

Another aspect of the present disclosure provides a compound comprising Formula (IV):

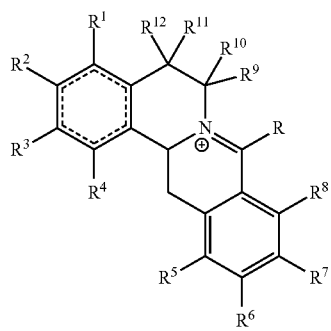

(IV)

wherein:

R is hydrogen, hydrocarbyl, or substituted hydrocarbyl;

$R^1$, $R^2$, $R^3$, and $R^4$ independently are hydrogen, halogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising $\{-\}O(CH_2)_nO\{-\}$;

$R^5$, $R^6$, $R^7$, and $R^8$ independently are hydrogen, halogen, $OR^{15}$, $NR^{15}N$ nitro, cyano, thiol, hydrocarbyl, substituted hydrocarbyl, or together $R^6$ and $R^7$ along with the ring carbons to which they are attached form a ring comprising $\{-\}O(CH_2)_nO\{-\}$;

$R^9$, $R^{10}$, $R^{11}$, $R^{12}$, $R^{15}$, and $R^{16}$ independently are hydrogen, hydrocarbyl, or substituted hydrocarbyl;

n is an integer from 1 to 3; and the dashed lines represent optional double bonds.

In some embodiments, R may be hydrogen, alkyl, heterocylic, aryl, heteroaryl, substituted alkyl, substituted heterocyclic, substituted aryl, or substituted heteroaryl. In various iterations, R may be lower alkyl, which is defined herein as $C_1$-$C_6$, and may be linear or cyclic. In other iterations, R may be morpholinyl, piperizinyl, phenyl, benzyl, pyridyl, pyridazinyl, pyranyl, oxazinyl, piperonyl, etc. Any of the foregoing may be substituted with at least one alkyl, alkenyl, alkynyl, aryl, halogen, oxo, keto, hydroxy, acyl, acyloxy, alkoxy, alkenoxy, alkynoxy, aryloxy, nitro, amino, amine, amide, thiol, cyano, ketal, acetal, ester, or ether.

In various embodiments $R^2$ and $R^3$ independently may be hydrogen, halogen, hydroxy, alkyoxy, alkyl or together $R^2$ and $R^3$ may form $\{-\}O-CH_2-O\{-\}$. In other embodiments, $R^5$ and $R^8$ independently may be hydrogen, halogen, hydroxy, alkoxy, or alkyl. In further embodiments, $R^6$ and $R^7$ independently may be hydrogen, halogen, hydroxy, alkoxy, alkyl, aryloxy, substituted aryloxy, nitro, amino, amine, or amide. In other embodiments, each of $R^9$, $R^{10}$, $R^{11}$, and $R^{12}$ may be hydrogen. In various embodiments, the ring containing the dashed lines may have one, two, or three double bonds. The configuration of C-14 may be R or S.

In specific embodiments, R may be heterocyclo, substituted heterocyclo, aryl, substituted aryl, heteroaryl, or substituted heteroaryl. In some embodiments, R may be phenyl, substituted phenyl, benzyl, or substituted benzyl. For example, the substituted phenyl or substituted benzyl may have at least one substituent chosen from halogen, hydroxy, alkoxy, alkyl, nitro, amino, or amine.

In one alternative of this embodiment, the compound comprising Formula (IV) may be a compound comprising Formula (IVa):

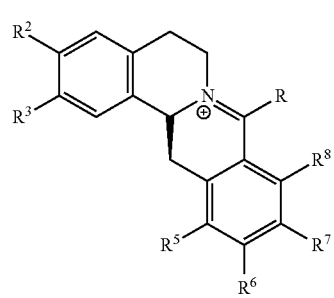

(IVa)

wherein:

R is hydrogen, alkyl, substituted alkyl, heterocyclo, substituted heterocyclo, aryl, substituted aryl, heteroaryl, or substituted heteroaryl;

$R^2$ is hydroxy or alkyoxy and $R^3$ is hydrogen, or together $R^2$ and $R^3$ form $\{-\}O-CH_2-O\{-\}$ $R^5$ and $R^8$ independently are hydrogen, halogen, hydroxy, alkoxy, or alkyl; and $R^6$ and $R^7$ independently hydrogen, halogen, hydroxy, alkyoxy, alkyl aryloxy, substituted aryloxy, nitro, amino, amine, or amide.

In another alternative of this embodiment, the compound comprising Formula (IV) may be a compound comprising Formula (IVb):

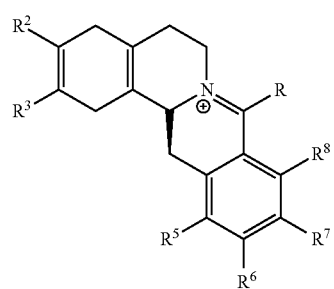

(IVb)

wherein:

R is hydrogen, alkyl, substituted alkyl, heterocyclo, substituted heterocyclo, aryl, substituted aryl, heteroaryl, or substituted heteroaryl;

$R^2$ is hydroxy or alkyoxy and $R^3$ is hydrogen, or together $R^2$ and $R^3$ form $\{-\}O-CH_2-O\{-\}$ $R^5$ and $R^8$ independently are hydrogen, halogen, hydroxy, alkoxy, or alkyl; and $R^6$ and $R^7$ independently hydrogen, halogen, hydroxy, alkyoxy, alkyl aryloxy, substituted aryloxy, nitro, amino, amine, or amide.

(c) Compounds Comprising Formula (V-1)

Still another aspect of the present disclosure provides a compound comprising Formula (V-1):

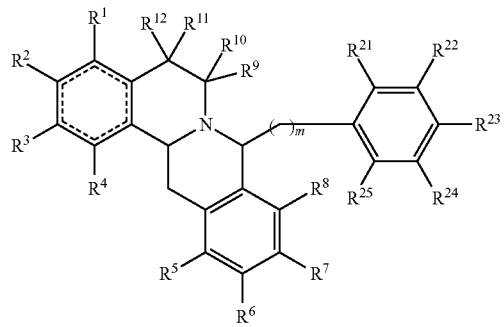

(V-1)

wherein:
- $R^1$, $R^2$, $R^3$, and $R^4$ independently are hydrogen, halogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising $\{-\}O(CH_2)_nO\{-\}$;
- $R^5$, $R^6$, $R^7$, and $R^8$ independently are hydrogen, halogen, $OR^{15}$, $NR^{15}N^{16}$, nitro, cyano, thiol, hydrocarbyl, substituted hydrocarbyl, or together $R^6$ and $R^7$ along with the ring carbons to which they are attached form a ring comprising $\{-\}O(CH_2)_nO\{-\}$; provided that at least two of $R^6$, $R^7$, and $R^8$ are other than methoxy;
- $R^9$, $R^{10}$, $R^{11}$, and $R^{12}$ independently are hydrogen, hydrocarbyl, or substituted hydrocarbyl;
- $R^{21}$, $R^{22}$, $R^{23}$, $R^{24}$, and $R^{25}$ independently are hydrogen, halogen, $OR^{15}$, $NR^{15}N^{16}$, nitro, cyano, thiol, hydrocarbyl, or substituted hydrocarbyl;
- $R^{15}$ and $R^{16}$ independently are hydrogen, hydrocarbyl, or substituted hydrocarbyl;
- m is an integer of 0 or greater;
- n is an integer from 1 to 3; and
- the dashed lines represent optional double bonds.

In some instances, $R^2$ and $R^3$ independently may be hydrogen, halogen, hydroxy, alkyoxy, alkyl or together $R^2$ and $R^3$ may form $\{-\}O-CH_2-O\{-\}$. In other embodiments, $R^5$ and $R^8$ independently may be hydrogen, halogen, hydroxy, alkoxy, or alkyl. In further embodiments, $R^6$ and $R^7$ independently may be hydrogen, halogen, hydroxy, alkoxy, alkyl, aryloxy, substituted aryloxy, nitro, amino, amine, or amide. In still other embodiments, $R^{21}$, $R^{22}$, $R^{23}$, $R^{24}$, and $R^{25}$ independently may be hydrogen, halogen, hydroxy, alkoxy, alkyl, nitro, amino, or amine. In additional embodiments, each of $R^9$, $R^{10}$, $R^{11}$, and $R^{12}$ may be hydrogen. In various embodiments, the ring containing the dashed lines may have one, two, or three double bonds. The configuration of each of C-14 and C-8 may be R or S. In exemplary embodiments, C-14 and C-8 have a syn stereochemistry.

In some embodiments, the compound comprising Formula (V-1) may be a compound comprising Formula (V-1a):

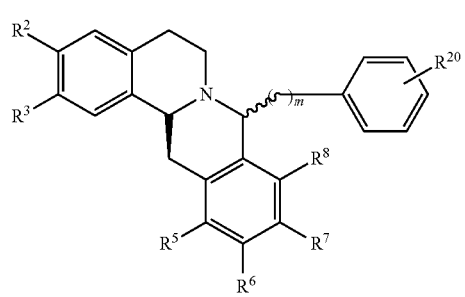

(V-1a)

wherein:
- $R^2$ is hydroxy or alkyoxy and $R^3$ is hydrogen, or together $R^2$ and $R^3$ form $\{-\}O-CH_2-O\{-\}$
- $R^5$ and $R^8$ independently are hydrogen, halogen, hydroxy, alkoxy, or alkyl;
- $R^6$ and $R^7$ independently hydrogen, halogen, hydroxy, alkyoxy, alkyl aryloxy, substituted aryloxy, nitro, amino, amine, or amide;
- $R^{20}$ is hydrogen, halogen, hydroxy, alkoxy, alkyl, nitro, amino, or amine; and
- m is 0 or 1.

In other embodiments, the compound comprising Formula (V-1) may be a compound comprising Formula (V-1b):

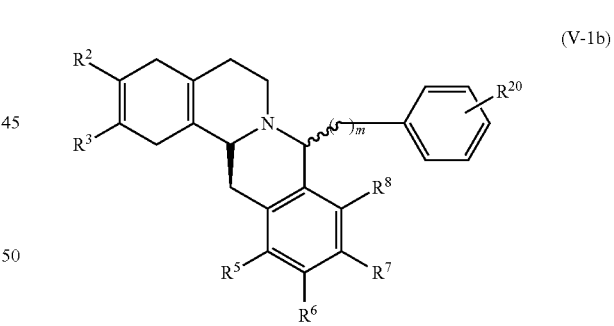

(V-1b)

wherein:
- $R^2$ is hydroxy or alkyoxy and $R^3$ is hydrogen, or together $R^2$ and $R^3$ form $\{-\}O-CH_2-O\{-\}$
- $R^5$ and $R^8$ independently are hydrogen, halogen, hydroxy, alkoxy, or alkyl;
- $R^6$ and $R^7$ independently hydrogen, halogen, hydroxy, alkyoxy, alkyl aryloxy, substituted aryloxy, nitro, amino, amine, or amide;
- $R^{20}$ is hydrogen, halogen, hydroxy, alkoxy, alkyl, nitro, amino, or amine; and
- m is 0 or 1.

Exemplary compounds comprising Formula (V-1a) are presented below:
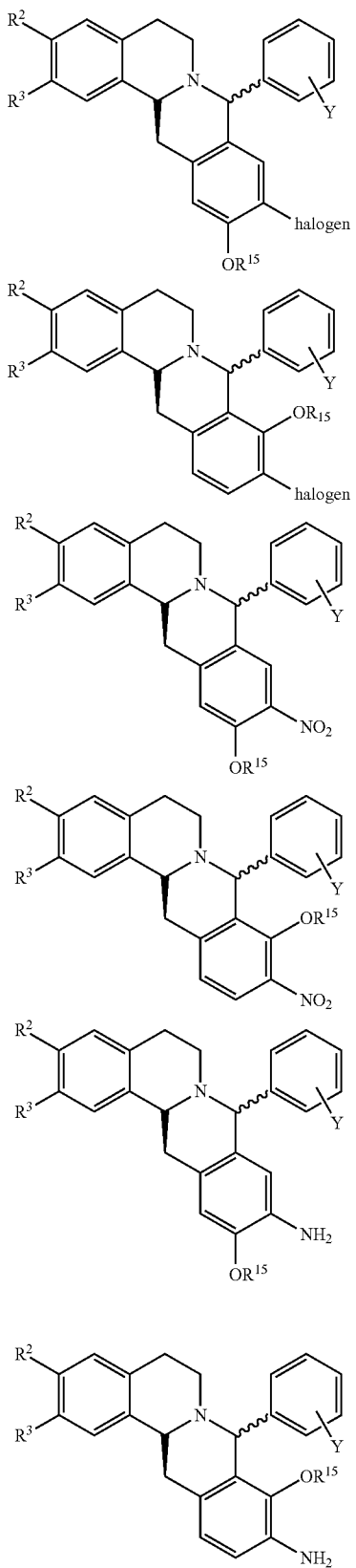
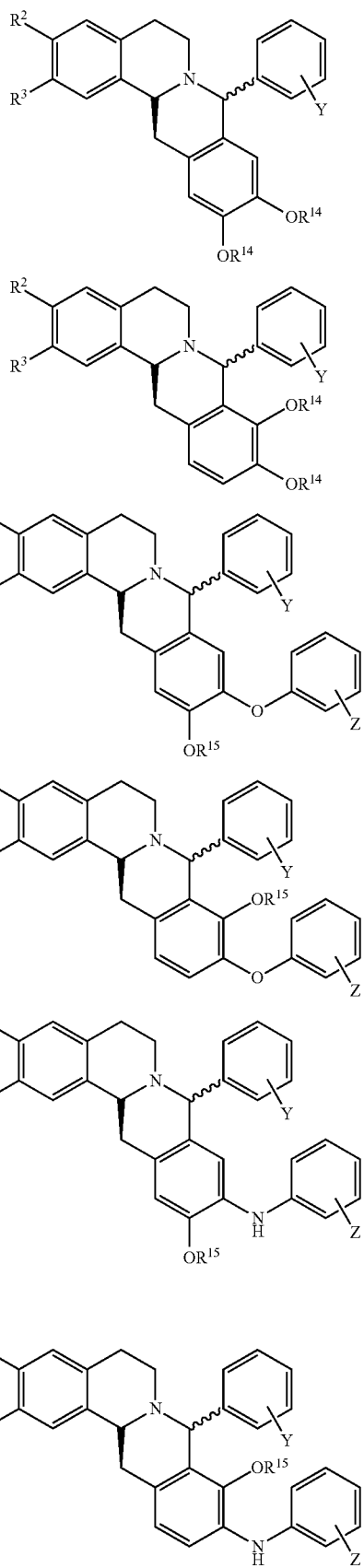

-continued

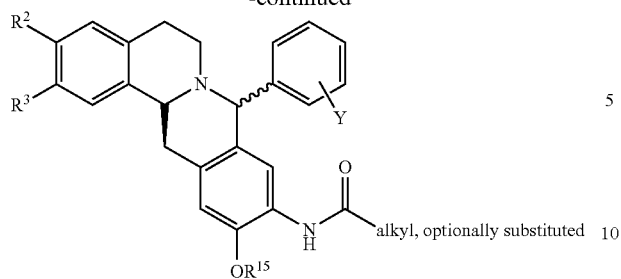

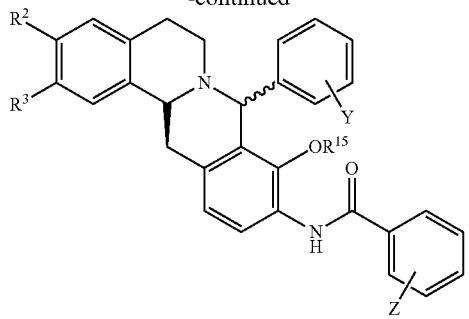

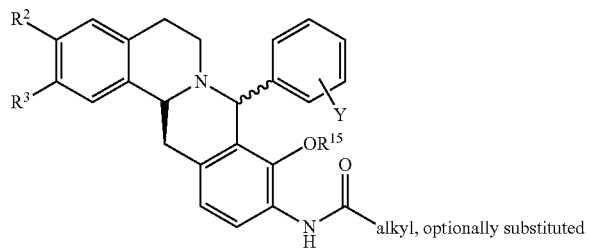

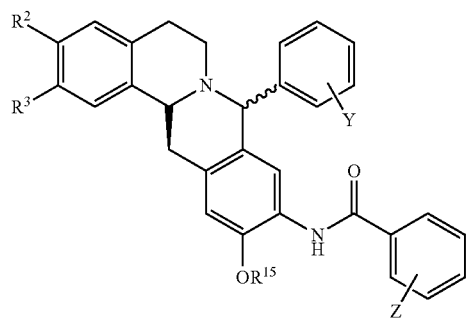

wherein:
R² is hydroxy or alkyoxy and R³ is hydrogen, or together R² and R³ form {—}O—CH₂—O{—}
R¹⁴ is hydrogen or C₂-C₆ alkyl
R¹⁵ is hydrogen or C₁-C₆ alkyl; and
Y and Z independently are hydrogen, halogen, hydroxy, alkoxy, alkyl, nitro, amino, or amine.

Those skilled in the art understand that the phenyl group at C-8 may be replaced with a benzyl group. Moreover, compounds comprising Formula (V-1 b) have similar exemplary compounds.

(II) Processes for Preparing Compounds Comprising Formula (V)

Another aspect of the present disclosure provides processes for the preparation of substituted berbine compounds. In general, the process entails formation of a new ring from an asymmetric compound. The process comprises contacting a compound comprising Formula (II) with a cyclizing agent to form a compound comprising Formula (III), which undergoes cyclization to form the compound comprising Formula (IV). The process further comprises contacting the compound comprising Formula (IV) with a reducing agent to form the berbine compound comprising Formula (V). For the purposes of illustration, Reaction Scheme 1 depicts the synthesis of the compound comprising Formula (V) in accordance with this aspect of the disclosure:

Reaction Scheme 1:

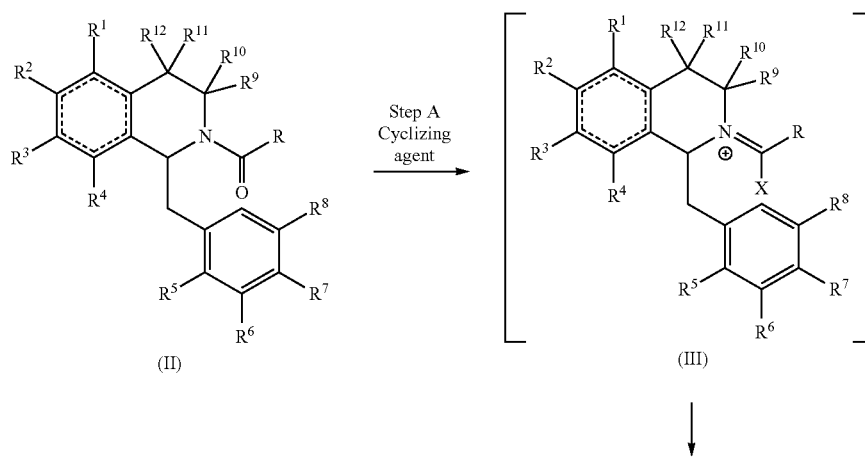

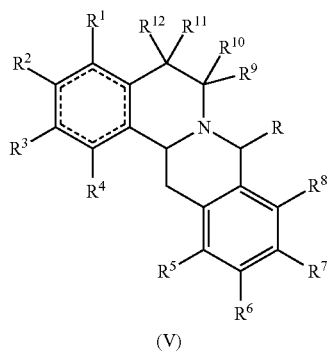

(V)

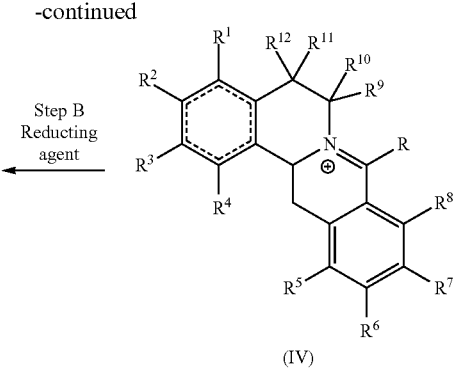

(IV)

wherein:
R is hydrogen, hydrocarbyl, or substituted hydrocarbyl;
$R^1$, $R^2$, $R^3$, and $R^4$ independently are hydrogen, halogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising $\{-\}O(CH_2)_nO\{-\}$;
$R^5$, $R^6$, $R^7$, and $R^8$ independently are hydrogen, halogen, $OR^{15}$, $NR^{15}N^{16}$, nitro, cyano, thiol, hydrocarbyl, substituted hydrocarbyl, or together $R^6$ and $R^7$ along with the ring carbons to which they are attached form a ring comprising $\{-\}O(CH_2)_nO\{-\}$;

$R^9$, $R^{10}$, $R^{11}$, and $R^{12}$ independently are hydrogen, hydrocarbyl, or substituted hydrocarbyl;
n is an integer from 1 to 3;
X is halogen, $\{-\}OSO_2R^{18}$, or $\{-\}OCOR^{18}$, wherein $R^{18}$ is hydrocarbyl or substituted hydrocarbyl; and
the dashed lines represent optional double bonds.

In some embodiments, a compound comprising Formula (Va) may be prepared by the process depicted in Reaction Scheme 1a:

Reaction Scheme 1a:

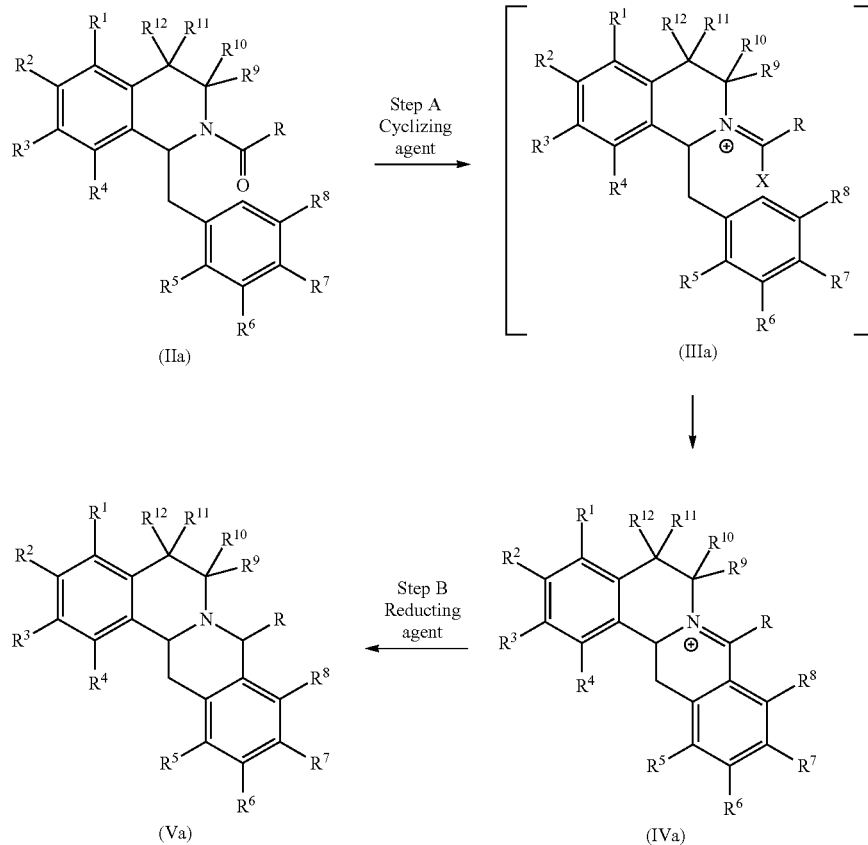

wherein the variables are as defined above.

In another embodiment, a compound comprising Formula (Vb) may be prepared by the process depicted in Reaction Scheme 1b:

Reaction Scheme 1b:

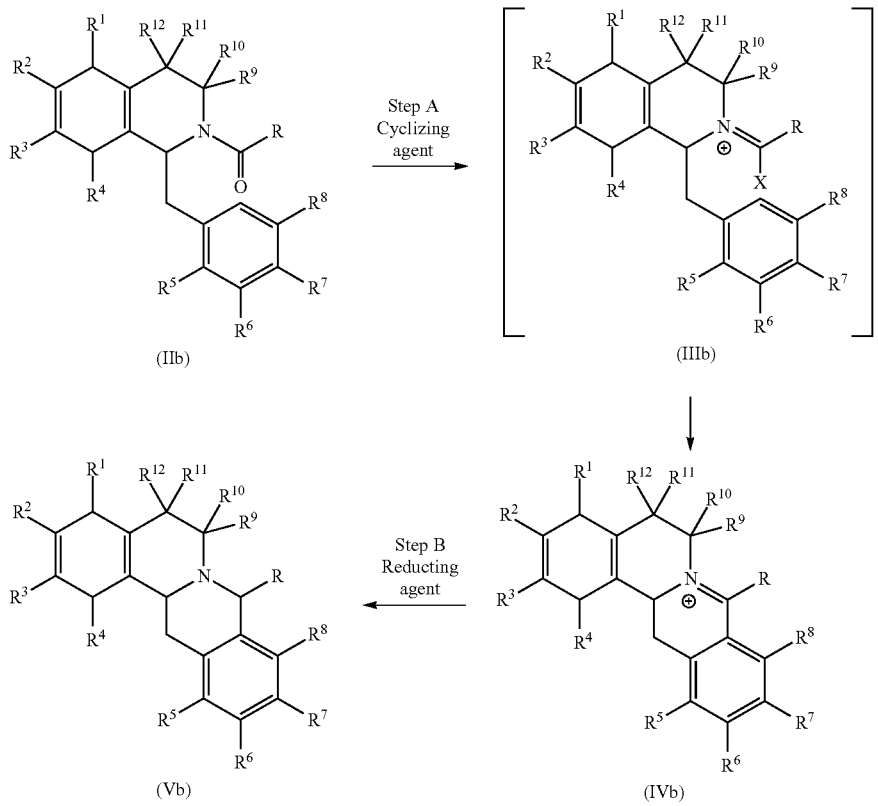

wherein the variables are as defined above.

In some embodiments, R may be hydrogen, alkyl, heterocylic, aryl, heteroaryl, substituted alkyl, substituted heterocyclic, substituted aryl, or substituted heteroaryl. In various iterations, R may be lower alkyl, which is defined herein as $C_1$-$C_6$, and may be linear or cyclic. In other iterations, R may be morpholinyl, piperizinyl, phenyl, benzyl, pyridyl, pyridazinyl, pyranyl, oxazinyl, piperonyl, etc. Any of the foregoing may be substituted with at least one alkyl, alkenyl, alkynyl, aryl, halogen, oxo, keto, hydroxy, acyl, acyloxy, alkoxy, alkenoxy, alkynoxy, aryloxy, nitro, amino, amine, amide, thiol, cyano, ketal, acetal, ester, or ether.

In various embodiments $R^2$ and $R^3$ independently may be hydrogen, halogen, hydroxy, alkyoxy, alkyl or together $R^2$ and $R^3$ may form {—}O—$CH_2$—O{—}. In other embodiments, $R^5$ and $R^8$ independently may be hydrogen, halogen, hydroxy, alkoxy, or alkyl. In further embodiments, $R^6$ and $R^7$ independently may be hydrogen, halogen, hydroxy, alkoxy, alkyl, aryloxy, substituted aryloxy, nitro, amino, amine, or amide. In other embodiments, each of $R^9$, $R^{10}$, $R^{11}$, and $R^{12}$ may be hydrogen. In various embodiments, the ring containing the dashed lines may have one, two, or three double bonds. In certain embodiments, X may be chloride, bromide, {—}$OSO_2$-trifluoromethane, {—}$OSO_2$-methane, or {—}$OSO_2$-toluene. The configuration of C-14 may be R or S.

(a) Step A—Reaction Mixture

Step A of the process comprises contacting a compound comprising Formula (II) with a cyclizing agent to form a compound comprising Formula (IV). This step of the process commences with formation of a reaction mixture. The reaction mixture comprises a compound comprising Formula (II), as detailed above.

(i) Cyclizing Agent

The reaction mixture further comprises a cyclizing agent. The cyclizing agent may be a phosphorous oxyhalide or an acid anhydride. The phosphorous oxyhalide may be phosphorous oxychloride ($POCl_3$), phosphorous oxybromide ($POBr_3$), or phosphorous oxyfluoride ($POF_3$). The cyclizing agent may be an inorganic acid anhydride, for example sulfur trioxide, solutions in sulfuric acid (i.e., fuming sulfuric acid or oleums), phosphorous pentoxide or mixtures of phosphorous pentoxide in phosphoric acid (i.e., polyphosphoric acid). The acid anhydride may also be an alkyl anhydride or an aryl anhydride. Non-limiting examples of suitable acid anhydrides include trifluoromethanesulfonic anhydride, methanesulfonic anhydride, p-toluenesulfonic anhydride, trifluoroacetic anhydride, acetic anhydride, acetic formic anhydride, benzoic anhydride, butyric anhydride, chlorophthalic anhydride, cyclopropylcarboxylic anhydride, cyclobutylcarboxylic anhydride, ethylenetetracarboxylic anhydride, formic anhydride, 2-furonic anhydride, gloxylic anhydride, maleic anhydride, malonic anhydride, methacrylic anhydride, nicotinic anhydride, oxalic anhydride, phthalic anhydride, propionic anhydride, succinic anhydride, toluic anhydride, and combinations thereof. In one embodiment, the acid anhydride may be trifluoromethanesulfonic anhydride.

The amount of the cyclizing agent added to the reaction mixture can and will vary. In general, the mole to mole ratio of the compound comprising Formula (II) to the cyclizing agent may range from about 1:0.5 to about 1:3. In various embodiments, the mole to mole ratio of the compound comprising Formula (II) to the cyclizing agent may range about 1:0.5 to about 1:1, from about 1:1 to about 1:1.5, from about 1:1.5 to about 1:2, from about 1:2 to about 1:2.5, or from about 1:2.5 to about 1:3. In exemplary embodiments, the mole to mole ratio of the compound comprising Formula (II) to the cyclizing agent may be from about 1:1 to about 1:2.

(ii) Solvent

The reaction mixture generally further comprises a solvent. The solvent may be an aprotic polar solvent, a protic polar solvent, a non-polar solvent, or combinations thereof. Suitable aprotic solvents include, without limit, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl) ether, N,N-dimethylacetamide (DMAC), N-methyl-2-pyrrolidinone (NMP), 1,4-dioxane, ethyl acetate, hexamethylphosphoramide, methyl acetate, methylene chloride, methoxyethane, nitrobenzene, nitromethane, propionitrile, propyl acetates, sulfolane, tetrahydrofuran (THF), 2-methyl tetrahydrofuran, tetrahydropyran, trichloromethane, and combinations thereof. Non-limiting examples of suitable protic polar solvents include diols such as propylene glycol, ethylene glycol, propanediol, and so forth; amides such as acetamide, benzamide, and the like; and combinations of any of the above. Non-limiting examples of suitable nonpolar solvents include benzene, butyl acetate, tert-butyl methyl ether, chlorobenzene, chloroform, chloromethane, cyclohexane, dichloromethane, dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, and combinations thereof. In exemplary embodiments, the solvent may be acetonitrile.

In general, the volume to mass ratio of the solvent to the compound comprising Formula (II) ranges from about 0.5:1 to about 100:1. In various embodiments, the volume to mass ratio of the solvent to the compound comprising Formula (II) may range from 0.5:1 to about 5:1, from about 5:1 to about 25:1, or from about 25:1 to about 100:1. In exemplary embodiments, the volume to mass ratio of the solvent to the compound comprising Formula (II) may range from about 5:1 to about 20:1.

(b) Step A—Reaction Conditions

In general, the reaction is conducted at a temperature that ranges from about 0° C. to about 120° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C., or from about 100° C. to about 120° C. The reaction may be conducted at a first temperature and then a second temperature. In exemplary embodiments, the temperature of the reaction may range from about 20° C. to about 60° C. The reaction generally is performed under ambient pressure.

Typically, the reaction is allowed to proceed for a sufficient period of time until the reaction is complete, as determined by chromatography (e.g., HPLC) or another suitable method. In this context, a "completed reaction" generally means that the reaction mixture contains a significantly diminished amount of the compound comprising Formula (II), and a significantly increased amount of the compound comprising Formula (IV) compared to the amounts of each present at the beginning of the reaction. Typically, the amount of the compound comprising Formula (II) remaining in the reaction mixture after the reaction is complete may be less than about 3%, or less than about 1%. In general, the reaction may proceed for about 2 hours to about 24 hours. In certain embodiments, the reaction may be allowed to proceed for about a period of time ranging from about 2 hours to about 4 hours, from about 4 hours to about 8 hours, from about 8 hours to about 12 hours, from about 12 hours to about 18 hours, or from about 18 hours to about 24 hours. In exemplary embodiments, the reaction may be allowed to proceed for about 10 hours to about 20 hours.

In general, the compound comprising Formula (IV) is not isolated from the reaction mixture. Accordingly, step (b) of the process may proceed in the same reaction pot or reactor. In some embodiments, however, the compound comprising Formula (IV) may be isolated from the reaction mixture using techniques known to those of skill in the art. Non-limiting examples of suitable techniques include precipitation, extraction, evaporation, distillation, chromatography, and crystallization.

The yield of the compound comprising Formula (IV) can and will vary. Typically, the yield of the compound comprising Formula (IV) will be at least about 40% by weight. In certain embodiments, the yield of the compound comprising Formula (IV) may be at least about 50%, at least about 60%, at least about 70%, at least about 80%, at least about 90%, or at least about 95%.

(c) Step B—Reaction Mixture

Step B of the process comprises contacting the compound comprising Formula (IV) with a reducing agent to form the compound comprising Formula (V).

A variety of reducing agents may be used in this step of the process. The reducing agent may be chiral or achiral. Non-limiting examples of suitable reducing agents for use in chemical reduction include hydrides (e.g., sodium borohydride, sodium cyanoborohydride, lithium aluminum hydride, diisobutylaluminum hydride, hydrogen iodide, hydrogen sulfide, and the like), phosphites, hypophosphites, sulfites, and combinations of a metal (e.g., tin, zinc, or iron) or a metal compound (e.g., chromium chloride, chromium acetate, and the like) with an organic or inorganic acid (e.g., formic acid, acetic acid, propionic acid, trifluoroacetic acid, p-toluenesulfonic acid, hydrochloric acid, and the like). In exemplary embodiments, the reducing agent may be sodium borohydride or sodium cyanoborohydride.

The amount of reducing agent used in this step of the process can and will vary. In general, the mole to mole ratio of the compound comprising Formula (II) to the reducing agent may range from about 1:0.5 to about 1:3. In various embodiments, the mole to mole ratio of the compound comprising Formula (II) to the reducing agent may range about 1:0.5 to about 1:1, from about 1:1 to about 1:1.5, from about 1:1.5 to about 1:2, from about 1:2 to about 1:2.5, or from about 1:2.5 to about 1:3. In exemplary embodiments, the mole to mole ratio of the compound comprising Formula (II) to the reducing agent may be from about 1:1 to about 1:2.

The reduction reaction generally is conducted in the presence of a solvent. Suitable solvents and ratios of solvent to the starting substrate are listed above in section (I)(a)(ii). The solvent may be the same as the solvent used in step A of the process. For example, the solvent may be carried over from step A and/or additional solvent may be added to the reaction mixture prior to step B of the process. Alternatively, the solvent used during step B of the process may be different from that used in step A of the process. In one embodiment, the solvent used during step B may be acetonitrile. In another embodiment, the solvent used during step B may be methanol or a mixture of methanol and water.

(d) Step B—Reaction Conditions

The temperature at which the reduction reaction is performed may vary. In general, the temperature of the reaction ranges from about 0° C. to about 120° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C., or from about 100°

C. to about 120° C. In exemplary embodiments, the temperature of the reaction may range from about 20° C. to about 60° C. For example, the reaction may be conducted at room temperature. The reaction generally is performed under ambient pressure.

Typically, the reaction is allowed to proceed for a sufficient period of time until the reaction is complete, as detailed above. In a completed reaction, the amount of the compound comprising Formula (IV) remaining in the reaction mixture may be less than about 3%, or less than about 1%. In general, the reaction may proceed for about 0.5 hour to about 72 hours. In some embodiments, the reaction may proceed for about 0.5 hour to about 4 hours, from about 4 hours to about 12 hours, from about 12 hours to about 24 hours, from about 24 hours to about 48 hours, or from about 48 hours to about 72 hours.

The compound comprising Formula (V) may be isolated from the reaction mixture using techniques known to those of skill in the art. Non-limiting examples of suitable techniques include precipitation, extraction, evaporation, distillation, chromatography, and crystallization.

Typically, the yield of the compound comprising Formula (V) will be at least about 40% by weight. In certain embodiments, the yield of the compound comprising Formula (V) may be at least about 60%, at least about 70%, at least about 80%, at least about 90%, or at least about 95%.

Each chiral carbon in the compounds described above may have an R configuration or an S configuration. That is, C-14 in the compounds comprising Formulas (II), (III), and (IV) may have an R or an S configuration. The configuration of C-8 and C-14 in the compound comprising Formula (V) may be RR, RS, SR, or SS. In particular embodiments, positions C-8 and C-14 of the compound comprising Formula (V) have a syn stereochemistry.

(e) Optional Additional Steps

Upon formation of the compound comprising Formula (V), the compound comprising Formula (V) may undergo additional reactions. For example, the $R^7$ (or $R^6$) group may be converted to an ether, an amine, or an amide.

(i) Synthesis of Ethers or Amines

In embodiments in which $R^7$ of the compound comprising Formula (V) is halogen, the compound comprising Formula (V) may be contacted with $R^{19}OH$ or $R^{19}NH_2$ to form a compound comprising Formula (VIa) or Formula (VIb), respectively, as shown in Reaction Scheme 2 below:

Reaction Scheme 2:

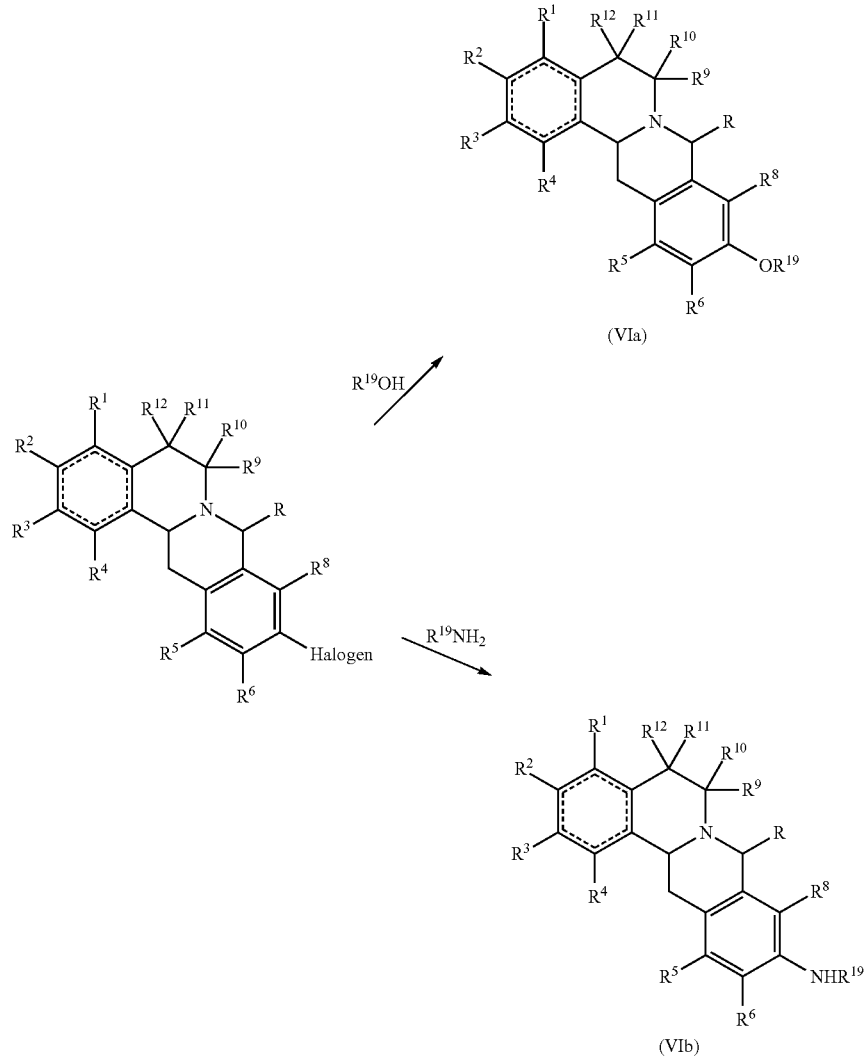

wherein:
R is hydrogen, hydrocarbyl, or substituted hydrocarbyl;
$R^1$, $R^2$, $R^3$, and $R^4$ independently are hydrogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising $\{-\}O(CH_2)_nO\{-\}$;
$R^5$, $R^6$, and $R^8$ independently are hydrogen, $OR^{15}$, $NR^{15}N^{16}$, nitro, cyano, thiol, hydrocarbyl, or substituted hydrocarbyl;
$R^9$, $R^{10}$, $R^{11}$, and $R^{12}$ independently are hydrogen, hydrocarbyl, or substituted hydrocarbyl;
$R^{19}$ is hydrocarbyl or substituted hydrocarbyl;
n is an integer from 1 to 3; and
the dashed lines represent optional double bonds.

A similar reaction may be used to generate compounds in which $R^6$ is the ether or amine. In such embodiments, $R^6$ in the compound comprising Formula (V) is halogen and $R^7$ is hydrogen, $OR^{15}$, $NR^{15}N^{16}$, nitro, cyano, thiol, hydrocarbyl, or substituted hydrocarbyl.

Reaction mixture. The reaction commences with the formation of a reaction mixture comprising the compound comprising (V) in which $R^7$ is halogen (e.g., chloro, bromo, or iodo) and an alcohol (i.e., $R^{19}OH$) or an amine (i.e., $R^{19}NH_2$). In some embodiments, $R^{19}$ may be alkyl, cycloalkyl, alkenyl, alkynyl, aryl, heteroaryl, substituted alkyl, substituted cycloalkyl, substituted alkenyl, substituted alkynyl, substituted aryl, or substituted heteroaryl. In other embodiments, $R^{19}$ may be $C_1$-$C_6$ alkyl, which may be substituted, linear or cyclic. In still other embodiments, $R^{19}$ may be aryl or aryl substituted with halo, nitro, hydroxyl, keto or oxo, $C_1$-$C_6$ alkyl, $C_1$-$C_6$ alkoxy, or $C_1$-$C_6$ alkenyl. Suitable aryl groups include phenyl, benzyl, pyridyl, pyrimidyl, pyrrolyl, and imidazolyl.

The amount of $R^{19}OH$ or $R^{19}NH_2$ added to the reaction mixture can and will vary. In general, the mole to mole ratio of the compound comprising Formula (V) to $R^{19}OH$ or $R^{19}NH_2$ may range from about 1:0.5 to about 1:20. In various embodiments, the mole to mole ratio of the compound comprising Formula (II) to $R^{19}OH$ or $R^{19}NH_2$ agent may range about 1:0.5 to about 1:1, from about 1:1 to about 1:2, from about 1:2 to about 1:5, from about 1:5 to about 1:10, or from about 1:10 to about 1:20. In exemplary embodiments, the mole to mole ratio of the compound comprising Formula (II) to $R^{19}OH$ or $R^{19}NH_2$ may be from about 1:1 to about 1:5.

The reaction mixture further comprises a transition metal catalyst. As used herein, the term "transition metal catalyst" refers to a transition metal element, transition metal salt, or a transition metal complex. In general, the transition metal may be any transition metal. In some embodiments, the transition metal may be iridium, iron, nickel, osmium, palladium, platinum, ruthenium and rhodium. In one exemplary embodiment, the transition metal may be ruthenium, iridium, or rhodium. A skilled artisan appreciates that the oxidation state of transition metal may vary, and may be, for example, (0), (I), (II), (III), (IV), (V), (VI) or (VII). For example, non-limiting examples of suitable transition metals include ruthenium(0), ruthenium (II), ruthenium(III), ruthenium(IV), rhodium(0), rhodium(I), rhodium(III), iridium(0), iridium(III), iridium(IV), palladium(0), palladium(II), palladium(IV), platinum(0), platinum(II), platinum(IV), and nickel(0).

In some embodiments, the transition metal catalyst may be the transition metal element itself. For example, the transition metal element may be a powder or a sponge, such as, e.g., ruthenium powder, rhodium powder, ruthenium sponge, rhodium sponge, palladium sponge, and so forth. Alternatively, the transition metal element may be rhodium black, ruthenium black, palladium black, etc. In still other embodiments, the transition metal element may be immobilized on a solid surface or support. Suitable examples include, but are not limited to, ruthenium on carbon, rhodium on carbon, palladium on carbon, ruthenium on alumina, rhodium on alumina, platinum on alumina, palladium on alumina, rhodium on silica, palladium on silica, palladium on charcoal, palladium on pumice, and so forth. In exemplary embodiments, the transition metal catalyst may be palladium supported on carbon.

In other embodiments, the transition metal catalyst may be a transition metal salt. Non-limiting examples of suitable salts include acetates, acetyacetonates, alkoxides, butyrates, carbonyls, dioxides, halides, hexonates, hydrides, mesylates, octanates, nitrates, nitrosyl halides, nitrosyl nitrates, sulfates, sulfides, sulfonates, phosphates, trifluoromethanesulfonates, trimethylacetates, tosylates, and combinations thereof. The transition metal salt may be soluble (i.e., homogeneous). Alternatively, the transition metal salt may be immobilized on a solid support (i.e., heterogeneous). The transition metal salt may be immobilized on the solid support via noncovalent or covalent bonds. In some embodiments, the solid support may be an inorganic material. Suitable inorganic materials include silicas, alumina, titania, carbondium, zirconia, activated charcoal, zeolites, clays, polymers, ceramics, and activated carbon. Suitable silicas include silicon dioxide, amorphous silica, and microporous or mesoporous silicas. In other embodiments, the solid support may be a polymer. The polymer may be a natural polymer, a synthetic polymer, a semi-synthetic polymer, or a copolymer. Non-limiting examples of polymers include agarose, cellulose, nitrocellulose, methyl cellulose, polyacrylic, polyacrylamide, polyacrylonitrile, polyamide, polyether, polyester, polyethylene, polystyrene, polysulfone, polyvinyl chloride, polyvinylidene, methacrylate copolymer, and polystyrene-vinyl chloride copolymer.

In further embodiments, the transition metal catalyst may be a transition metal complex. In general, a transition metal complex comprises the transition metal and 4, 5, or 6 coordinate species with oxidation states ranging from 0 to 8. The complexes may be ionic, or the complexes may comprise covalently bound ligands and counter ions. Alternatively, the complexes may comprise a mixture of ionic and covalent bonds between the metal, ligand(s), and/or counter ion(s). The ligand may be monodentate or polydentate. Non-limiting examples of suitable ligands include arene ligands, olefin ligands, alkyne ligands, heterocycloalkyl ligands, heteroaryl ligands, alkyl ligands, cyclopentadienyl ligands, hydride ligands, amine ligands, carbonyl ligands, nitrogen donor ligands, phosphorous donor ligands, oxygen donor ligands, and so forth. The ligand may also be a solvent such as, e.g., DMSO, methanol, methylene chloride, tetrahydrofuran, acetone, ethanol, pyridine, or a tetraalkylammonia compound. Suitable counter ions include, but are not limited to, halides, $BF_4$, $PF_6$, $ClO_4$, $CHO_2$, $CF_3SO_3$, $CH_3CO_2$, $ArCO_2$, $CH_3SO_3$, p-tolylSO$_3$, $HSO_4$, $H_2PO_4$, and hydrocarbyl anions. Numerous transition metal complexes are detailed in "Transposition of Allylic Alcohols into Carbonyl Compounds Mediated by Transition Metal Complexes" by Uma et al., Chem. Rev. 103: 27-51 (2003).

In exemplary embodiments, the transition metal catalyst may comprise palladium. Non-limiting examples of palladium catalysts include Pd(acac)$_2$, [Pd(allyl)Cl]$_2$, Pd(MeCN)$_2$Cl$_2$, Pd(dba)$_2$, Pd(TFA)$_2$, Pd$_2$(dba)$_3$·CHCl$_3$, Pd(PPh$_3$)$_4$, Pd(OAc)$_2$, Pd(PCy$_3$)$_2$Cl$_2$, Pd(PPh$_3$)$_2$Cl$_2$, Pd[P(o-tol)$_3$]$_2$Cl$_2$, Pd(amphos)Cl$_2$, Pd(dppf)Cl$_2$, Pd(dtpf)Cl$_2$, Pd(MeCN)$_4$(BF$_4$)$_2$, PdBr$_2$, PdCl$_2$, (SPhos) Pd(II) phenethylamine chloride, (XPhos) Pd(II) phenethylamine chloride, (RuPhos) Pd(II) phenethylamine chloride, (t-BuXPhos) Pd(II) phenethylamine chloride, and (BrettPhos) Pd(II) phenethylamine chloride.

The amount of transition metal catalyst added to the reaction mixture can and will vary. In general, the amount of transition metal catalyst added to the reaction mixture may range from about 0.005% to about 10% by weight. In various embodiments, the amount of transition metal catalyst added to the reaction mixture may range from about 0.005% to about 0.05%, from about 0.05% to about 0.5%, from about 0.5% to about 2%, or from about 2% to about 10% by weight. In certain embodiments, the amount of transition metal catalyst added to the reaction mixture may range from about 0.01% to about 1% by weight.

The reaction mixture further comprises a proton acceptor. Suitable proton acceptors include borate salts (such as, for example, $NaBO_3$), di- and tri-basic phosphate salts (such as, for example, $Na_2HPO_4$ and $Na_3PO_4$, and the like), bicarbonate salts (such as, for example, $NaHCO_3$, $KHCO_3$, $LiHCO_3$, and so forth), carbonate salts (such as, for example, $Na_2CO_3$, $K_2CO_3$, $Li_2CO_3$, and the like), butoxides (such as, e.g., sodium tert-butoxide, potassium tert-butoxide), organic bases (such as, for example, pyridine, triethylamine, diisopropylethylamine, N-methylmorpholine, N,N-dimethylaminopyridine), and mixtures thereof. In exemplary embodiments, the proton acceptor may be sodium tert-butoxide, $K_2CO_3$, or triethylamine.

The amount of proton acceptor added to the reaction mixture may vary. In general, the mole to mole ratio of the compound comprising Formula (V) to the proton acceptor may range from about 1:0.5 to about 1:10. In various embodiments, the mole to mole ratio of the compound comprising Formula (V) to the proton acceptor may range from about 1:0.5 to about 1:2, from about 1:2 to about 1:5, or from about 1:5 to about 1:10. In exemplary embodiments, the mole to mole ratio of the compound comprising Formula (V) to the proton acceptor may range from about 1:1 to about 1:4.

The reaction mixture also comprises a solvent. Suitable solvents include aprotic polar solvents, non-polar solvents, or combinations thereof. Examples of aprotic polar solvents and non-polar solvents are presented above in section (II)(a)(ii). In exemplary embodiments, the solvent may be toluene, tetrahydrofuran (THF), N,N-dimethylformamide (DMF), or, N,N-dimethylacetamide (DMAC), In general, the volume to mass ratio of the solvent to the compound comprising Formula (V) may range from about 0.5:1 to about 100:1. In various embodiments, the volume to mass ratio of the solvent to the compound comprising Formula (V) may range from 0.5:1 to about 5:1, from about 5:1 to about 25:1, or from about 25:1 to about 100:1. In exemplary embodiments, the volume to mass ratio of the solvent to the compound comprising Formula (V) may range from about 5:1 to about 20:1.

Reaction conditions. The temperature at which the reaction is conducted may vary depending upon the identity of the solvent and the nature of the substituents on the compound comprising Formula (V). In general, the temperature of the reaction may range from about 0° C. to about 200° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C., from about 100° C. to about 120° C., from about 120° C. to about 150° C., or from about 150° C. to about 200° C. In specific embodiments, the reaction may be conducted at a temperature ranging from room temperature to reflux. The reaction generally is performed under ambient pressure.

Typically, the reaction is allowed to proceed for a sufficient period of time until the reaction is complete, as detailed above. In a completed reaction, the amount of the compound comprising Formula (V) remaining in the reaction mixture may be less than about 3%, or less than about 1%. In general, the reaction may proceed for about 1 hour to about 72 hours. In some embodiments, the reaction may proceed for about 1 hour to about 4 hours, from about 4 hours to about 12 hours, from about 12 hours to about 24 hours, from about 24 hours to about 48 hours, or from about 48 hours to about 72 hours.

The compound comprising Formula (VIa) or (VIb) may be isolated from the reaction mixture using techniques known to those of skill in the art. Non-limiting examples of suitable techniques include precipitation, extraction, evaporation, distillation, chromatography, and crystallization.

Typically, the yield of the compound comprising Formula (VIa) or (VIb) will be at least about 40% by weight. In certain embodiments, the yield of the compound comprising Formula (VIa) or (VIb) may be at least about 60%, at least about 70%, at least about 80%, at least about 90%, or at least about 95%.

(ii) Synthesis of Amides

In embodiments in which $R^7$ of the compound comprising Formula (V) is $NH_2$, the compound comprising Formula (V) may be contacted $R^{19}C(O)X'$ to form a compound comprising Formula (VIc) according to Reaction Scheme 3:

Reaction Scheme 3:

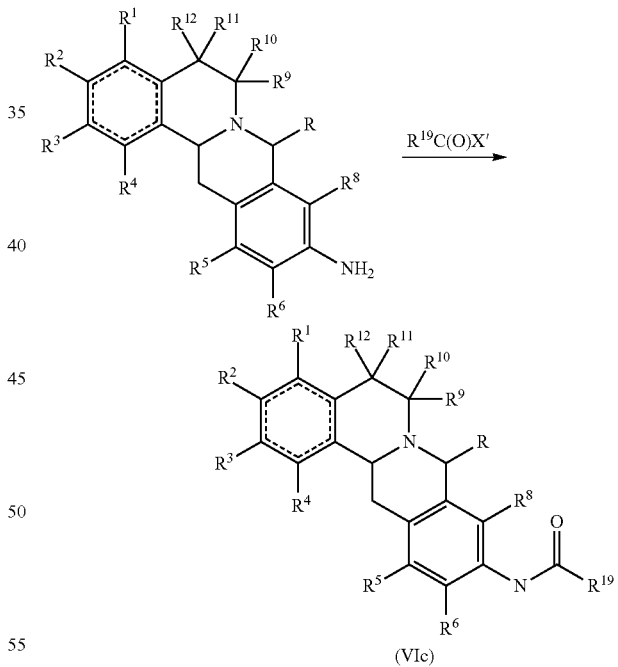

wherein:
R is hydrogen, hydrocarbyl, or substituted hydrocarbyl;
$R^1$, $R^2$, $R^3$, and $R^4$ independently are hydrogen, halogen, $OR^{15}$, amine, nitro, cyano, thiol, hydrocarbyl, substituted hydrocarbyl, or together $R^2$ and $R^3$ along with the ring carbons to which they are attached form a ring comprising $\{-\}O(CH_2)_nO\{-\}$;
$R^5$, $R^6$, and $R^8$ independently are hydrogen, halogen, $OR^{15}$, amine, nitro, cyano, thiol, hydrocarbyl, or substituted hydrocarbyl;

$R^9$, $R^{10}$, $R^{11}$, $R^{12}$, and $R^{15}$ independently are hydrogen, hydrocarbyl, or substituted hydrocarbyl;

$R^{19}$ is hydrocarbyl or substituted hydrocarbyl;

X' is halogen;

n is an integer from 1 to 3; and the dashed lines represent optional double bonds.

In other embodiments, $R^7$ in the compound comprising Formula (V) may be $NO_2$, which can be reduced to $NH_2$ by contact with a hydrogen source (e.g., gaseous hydrogen and a suitable catalyst, e.g., palladium on carbon).

A similar reaction may be used to generate compound in which $R^6$ is the amide. In such embodiments, $R^6$ in the compound comprising Formula (V) is $NH_2$ (or $NO_2$) and $R^7$ is hydrogen, halogen, $OR^{15}$, amine, cyano, thiol, hydrocarbyl, or substituted hydrocarbyl.

Reaction mixture. The reaction commences with the formation of a reaction mixture comprising the compound comprising (V) in which $R^7$ is $NH_2$ and an acyl halide (e.g., $R^{19}C(O)X'$). In some embodiments, $R^{19}$ may be alkyl, cycloalkyl, alkenyl, alkynyl, aryl, heteroaryl, substituted alkyl, substituted cycloalkyl, substituted alkenyl, substituted alkynyl, substituted aryl, or substituted heteroaryl. In certain embodiments, $R^{19}$ may be $C_1$-$C_6$ alkyl, which may be substituted, linear or cyclic. In other embodiments, $R^{19}$ may be aryl or aryl substituted with halo, nitro, hydroxyl, keto or oxo, $C_1$-$C_6$ alkyl, $C_1$-$C_6$ alkyoxy, or $C_1$-$C_6$ alkenyl. Suitable aryl groups include phenyl, benzyl, pyridyl, pyrimidyl, pyrrolyl, and imidazolyl.

A variety of acyl halides are suitable for use in this reaction. Suitable acyl halides include, without limit, alkyl acyl halides (such as, e.g., formyl halide, acetyl halide, propionyl halide, butyryl halide, hexanoyl halide, cyclopentane carbonyl halide, and the like) and aryl acyl halides (such as, e.g., benzoyl halide, phenyl acetyl halide, phenyl haloformate, toluoyl halide, toluenesulfonyl halide, 2-furoyl halide, nicotinoyl halide, piperonyloyl halide, and so forth).

The amount of acyl halide utilized in the reaction can and will vary. In general, the mole to mole ratio of the compound comprising Formula (V) to the acyl halide may range from about 1:0.8 to about 1:2. In various embodiments, the mole to mole ratio of the compound comprising Formula (V) to the acyl halide may range from about 1:0.8 to about 1:1.0, from about 1:1.0 to about 1:1.2, from about 1:1.2 to about 1:1.4, from about 1:1.4 to about 1:1.8, or from about 1:1.8 to about 1:2. In exemplary embodiments, the mole to mole ratio of the compound comprising Formula (V) to the acyl halide may range from about 1:1.0 to about 1:1.2.

The reaction mixture further comprises a proton acceptor. Suitable proton acceptors include borate salts (such as, for example, $NaBO_3$), di- and tri-basic phosphate salts (such as, for example, $Na_2HPO_4$ and $Na_3PO_4$, and the like), bicarbonate salts (such as, for example, $NaHCO_3$, $KHCO_3$, $LiHCO_3$, and so forth), carbonate salts (such as, for example, $Na_2CO_3$, $K_2CO_3$, $Li_2CO_3$, and the like), butoxides (such as, e.g., sodium tert-butoxide, potassium tert-butoxide), organic bases (such as, for example, pyridine, triethylamine, diisopropylethylamine, N-methylmorpholine, N,N-dimethylaminopyridine), and mixtures thereof. In exemplary embodiments, the proton acceptor may be triethylamine, diisopropylethylamine, or N-methylmorpholine.

The amount of proton acceptor added to the reaction mixture may vary. In general, the mole to mole ratio of the compound comprising Formula (V) to the proton acceptor ranges from about 1:0.5 to about 1:10. In various embodiments, the mole to mole ratio of the compound comprising Formula (V) to the proton acceptor may range from about 1:0.5 to about 1:2, from about 1:2 to about 1:5, or from about 1:5 to about 1:10. In exemplary embodiments, the mole to mole ratio of the compound comprising Formula (V) to the proton acceptor may range from about 1:1 to about 1:4.

The reaction mixture also comprises a solvent. Suitable solvents include aprotic polar solvents, non-polar solvents, or combinations thereof. Examples of aprotic polar solvents and non-polar solvents are presented above in section (II)(a)(ii). In exemplary embodiments, the solvent may be tetrahydrofuran, acetonitrile, dichloromethane, or chloroform.

In general, the volume to mass ratio of the solvent to the compound comprising Formula (V) may range from about 0.5:1 to about 100:1. In various embodiments, the volume to mass ratio of the solvent to the compound comprising Formula (V) may range from 0.5:1 to about 5:1, from about 5:1 to about 25:1, or from about 25:1 to about 100:1. In exemplary embodiments, the volume to mass ratio of the solvent to the compound comprising Formula (V) may range from about 5:1 to about 20:1.

Reaction conditions. The temperature at which the reaction is conducted can and will may. In general, the temperature of the reaction may range from about –50° C. to about 50° C. In various embodiments, the temperature of the reaction may range from about –500° C. to about –20° C., from about –20° C. to about 0° C., from about 0° C. to about 20° C., or from about 20° C. to about 50° C. In specific embodiments, the reaction may be conducted at room temperature. The reaction generally is performed under ambient pressure.

Typically, the reaction is allowed to proceed for a sufficient period of time until the reaction is complete, as detailed above. In a completed reaction, the amount of the compound comprising Formula (V) remaining in the reaction mixture may be less than about 3%, or less than about 1%. In general, the reaction may proceed for about 1 hour to about 72 hours. In some embodiments, the reaction may proceed for about 1 hour to about 4 hours, from about 4 hours to about 12 hours, from about 12 hours to about 24 hours, from about 24 hours to about 48 hours, or from about 48 hours to about 72 hours.

The compound comprising Formula (VIc) may be isolated from the reaction mixture using techniques known to those of skill in the art. Non-limiting examples of suitable techniques include precipitation, extraction, evaporation, distillation, chromatography, and crystallization.

Typically, the yield of the compound comprising Formula (VIc) will be at least about 40% by weight. In certain embodiments, the yield of the compound comprising Formula (VIc) may be at least about 60%, at least about 70%, at least about 80%, at least about 90%, or at least about 95%.

(III) Process for Preparing a Compound Comprising Formula (II)

A further aspect of the present disclosure encompasses a process for preparing a compound comprising Formula (II). The process comprises contacting a compound comprising Formula (I) with a carbonyl donor for preparing a compound of Formula (V) may comprise contacting a compound of Formula (I) with a carbonyl donor to form the compound comprising Formula (II), according to Reaction Scheme 4 below:

Reaction Scheme 4:

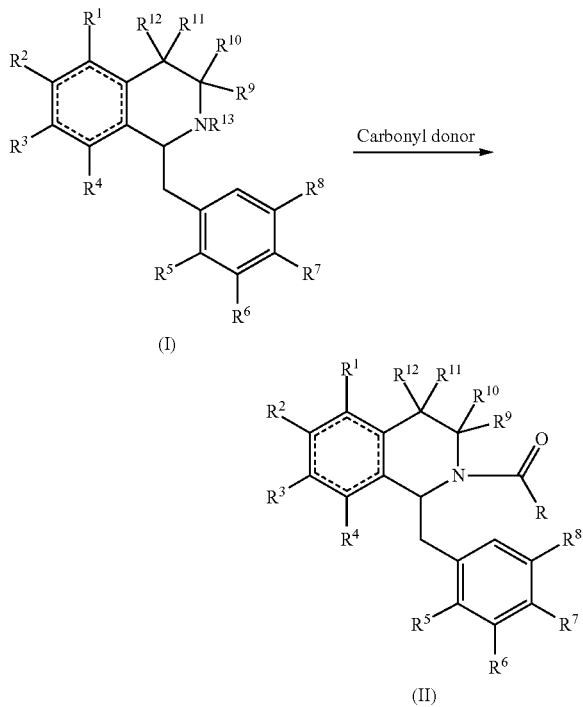

(I)

(II)

wherein:
R is hydrogen, hydrocarbyl, or substituted hydrocarbyl;
$R^1$ $R^2$, $R^3$, and $R^4$ independently are hydrogen, halogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising {—}O(CH$_2$)$_n$O{—};
$R^5$, $R^6$, $R^7$, and $R^8$ independently are hydrogen, halogen, $OR^{15}$, $NR^{15}N^{16}$, nitro, cyano, thiol, hydrocarbyl, substituted hydrocarbyl, or together $R^6$ and $R^7$ along with the ring carbons to which they are attached form a ring comprising {—}O(CH$_2$)$_n$O{—};
$R^9$, $R^{10}$, $R^{11}$, $R^{12}$, $R^{13}$, $R^{15}$, and $R^{16}$ independently are hydrogen, hydrocarbyl, or substituted hydrocarbyl;
n is an integer from 1 to 3; and
the dashed lines represent optional double bonds.

In some embodiments, R may be hydrogen, alkyl, heterocylic, aryl, heteroaryl, substituted alkyl, substituted heterocyclic, substituted aryl, or substituted heteroaryl. In various iterations, R may be lower alkyl, which is defined herein as $C_1$-$C_6$, and may be linear or cyclic. In other iterations, R may be morpholinyl, piperizinyl, phenyl, benzyl, pyridyl, pyridazinyl, pyranyl, oxazinyl, piperonyl, etc. Any of the foregoing may be substituted with at least one alkyl, alkenyl, alkynyl, aryl, halogen, oxo, keto, hydroxy, acyl, acyloxy, alkoxy, alkenoxy, alkynoxy, aryloxy, nitro, amino, amine, amide, thiol, cyano, ketal, acetal, ester, or ether.

In various embodiments $R^2$ and $R^3$ independently may be hydrogen, halogen, hydroxy, alkyoxy, alkyl or together $R^2$ and $R^3$ may form {—}O—CH$_2$—O{—}. In other embodiments, $R^5$ and $R^8$ independently may be hydrogen, halogen, hydroxy, alkoxy, or alkyl. In further embodiments, $R^6$ and $R^7$ independently may be hydrogen, halogen, hydroxy, alkoxy, alkyl, aryloxy, substituted aryloxy, nitro, amino, amine, or amide. In some embodiments, $R^{13}$ may be hydrogen, alkyl, aryl, substituted alkyl, or substituted aryl. In other embodiments, each of $R^9$, $R^{10}$, $R^{11}$, and $R^{12}$ may be hydrogen. In various embodiments, the ring containing the dashed lines may have one, two, or three double bonds. The configuration of C-14 may be R or S.

(a) Reaction Mixture

The process commences with formation of a reaction mixture. The reaction mixture comprises the compound comprising Formula (I) as detailed above.

(i) Carbonyl Donor

The reaction mixture further comprises a carbonyl donor. A variety of carbonyl donors are suitable for use in this process. In some embodiments, the carbonyl donor may be an acyl halide, i.e., R'C(O)X, wherein R' is hydrocarbyl or substituted hydrocarbyl and X is halogen (and wherein R' is transferred along with the carbonyl to the compound comprising Formula (II)). In other embodiments, the carbonyl donor may be a formate, i.e., R"OC(O)H, wherein R" is hydrocarbyl or substituted hydrocarbyl (and wherein H is transferred along with the carbonyl to the compound comprising Formula (II)). In further embodiments, the carbonyl donor may be an aldehyde, i.e., R'CHO, wherein R' is hydrocarbyl or substituted hydrocarbyl (and wherein R' is transferred along with the carbonyl to the compound comprising Formula (II)).

In some embodiments the carbonyl donor may be an acyl halide. Non-limiting examples of suitable acyl halides include alkyl acyl halides (such as, e.g., formyl halide, acetyl halide, propionyl halide, butyryl halide, hexanoyl halide, cyclopentane carbonyl halide, and the like) and aryl acyl halides (such as, e.g., benzoyl halide, substituted benzoyl halide, phenyl acetyl halide, phenyl haloformate, toluoyl halide, toluenesulfonyl halide, 2-furoyl halide, nicotinoyl halide, piperonyloyl halide, and so forth). The amount of acyl halide added to the reaction mixture may vary. In general, the mole to mole ratio of the compound comprising Formula (I) to the acyl halide may range from about 1:0.5 to about 1:4. In various embodiments, the mole to mole ratio of the compound comprising Formula (I) to the acyl halide may range from about 1:0.1 to about 1:1, from about 1:1 to about 1:2, from about 1:2 to about 1:3, or from about 1:3 to about 1:4. In exemplary embodiments, the mole to mole ratio of the compound comprising Formula (I) to the acyl halide may range from about 1:1 to about 1:2.

In other embodiments, the carbonyl donor may be a formate. Non-limiting examples of suitable aldehydes include methyl formate, ethyl formate, propyl formate, butyl formate, pentyl formate, hexyl formate, phenyl formate, benzyl formate, and so forth. The amount of formate contacted with the compound comprising Formula (I) can and will vary. In general, the mole to mole ratio of the compound comprising Formula (I) to the formate may range from about 1:5 to about 1:50. In certain embodiments, the mole to mole ratio of the compound comprising Formula (I) to the formate may range from about 1:5 to about 1:10, from about 1:10 to about 1:30, or from about 1:30 to about 1:50. In exemplary embodiments, the mole to mole ratio of the compound comprising Formula (I) to the formate may range from about 1:10 to about 1:30.

In additional embodiments, the carbonyl donor may be an aldehyde. Non-limiting examples of suitable aldehydes include formaldehyde, acetaldehyde, propionaldehyde, butyraldehyde, cyclopropane carboxaldehyde, cyclobutane carboxaldehyde, benzaldehyde, glyoxal, glyoxylic acid, 2-furaldehyde, nicotinaldehyde, and so forth. The amount of aldehyde added to the reaction mixture may vary. In general, the mole to mole ratio of the compound comprising Formula (I) to the aldehyde may range from about 1:0.2 to about 1:4. In various embodiments, the mole to mole ratio of the compound comprising Formula (I) to the aldehyde may range from about 1:0.1 to about 1:1, from about 1:1 to about 1:2, from about 1:2 to about 1:3, or from about 1:3 to about 1:4. In exemplary embodiments, the mole to mole ratio of the compound comprising Formula (I) to the aldehyde may range from about 1:0.5 to about 1:2.

(ii) Optional Proton Acceptor or Proton Donor

Depending upon the carbonyl donor used, the reaction mixture may further comprise a proton acceptor or proton donor. In embodiments in which the carbonyl donor is an acyl halide, the reaction mixture may further comprise a proton acceptor. The proton acceptor typically has a pKa between about 7 and about 13. Suitable proton acceptors having this characteristic include borate salts (such as, for example, $NaBO_3$), di- and tri-basic phosphate salts (such as, for example, $Na_2HPO_4$ and $Na_3PO_4$, and the like), bicarbonate salts (such as, for example, $NaHCO_3$, $KHCO_3$, $LiCO_3$, and the like), carbonate salts (such as, for example, $Na_2CO_3$, $K_2CO_3$, $Li_2CO_3$, and the like), organic bases (such as, for example, pyridine, triethylamine, diisopropylethylamine, N-methylmorpholine, N,N-dimethylaminopyridine), and mixtures of any of the above. In exemplary embodiments, the proton acceptor may be triethylamine.

The amount of proton acceptor added to the reaction mixture comprising an acyl halide may vary. In general, the mole to mole ratio of the compound comprising Formula (I) to the proton acceptor ranges from about 1:0.5 to about 1:10. In various embodiments, mole to mole ratio of the compound comprising Formula (I) to the proton acceptor may range from about 1:0.5 to about 1:2, from about 1:2 to about 1:5, or from about 1:5 to about 1:10. In exemplary embodiments, the mole to mole ratio of the compound comprising Formula (I) to the proton acceptor may range from about 1:1 to about 1:4.

In embodiments in which the carbonyl donor is an aldehyde, the reaction mixture may further comprise a proton acceptor or a proton donor. In general, the proton donor or proton acceptor has a pKa of less than about 9. Suitable proton donors include, but are not limited to, HOAc, $HCO_2H$, n-$PrCO_2H$, $PhCO_3H$, $MeSO_3H$, poly $H_3PO_4$, $H_3PO_4$, $H_2SO_4$, HCl, HBr, $H_1$, $CF_3SO_3H$, p-methyltoluenesulfonic acid, and combinations thereof. Suitable proton acceptors include borate salts (such as, for example, $NaBO_3$), di- and tri-basic phosphate salts (such as, for example, $Na_2HPO_4$ and $Na_3PO_4$, and the like), bicarbonate salts (such as, for example, $NaHCO_3$, $KHCO_3$, $LiHCO_3$, and so forth), carbonate salts (such as, for example, $Na_2CO_3$, $K_2CO_3$, $Li_2CO_3$, and the like), butoxides (such as, e.g., sodium tert-butoxide, potassium tert-butoxide), organic bases (such as, for example, pyridine, triethylamine, diisopropylethylamine, N-methylmorpholine, N,N-dimethylaminopyridine), and mixtures thereof. Other suitable proton acceptors/proton donors include N,N-bis-(2-hydroxyethyl)-glycine (BICINE), N-[tris(hydroxymethyl)methyl]glycine (TRICINE), tris(hydroxymethyl)aminomethane (TRIS), 3-(cyclohexylamino)-1-propanesulfonic acid (CAPS), 3-(cyclohexylamino)-2-hydroxy-1-propanesulfonic acid (CAPSO), N-(2-hydrooxyethyl)piperazine-N'-(3-propanesulfonic acid) (EPPS), N2-hydroxyethylpiperazine-N'-2-ethanesulfonic acid (HEPES), 2-(N-morpholino)ethanesulfonic acid (MES), 3-(N-morpholino)propanesulfonic acid (MOPS), piperazine-N,N'-bis(2-ethanesulfonic acid) (PIPES), 3-{[tris(hydroxymethyl)]amino}-1-propanesulfonic acid (TAPS), and N-tris(hydroxymethyl)methyl-2-amino-ethanesulfonic acid (TES).

The amount of proton acceptor or proton donor added to the reaction mixture comprising an aldehyde may vary. In general, the mole to mole ratio of the of the compound comprising Formula (I) to the proton acceptor ranges from about 1:0.05 to about 1:10. In various embodiments, mole to mole ratio of the compound comprising Formula (I) to the proton acceptor or proton donor may range from about 1:0.05 to about 1:1, from about 1:1 to about 1:5, or from about 1:5 to about 1:10. In exemplary embodiments, the mole to mole ratio of the compound comprising Formula (I) to the proton acceptor or proton donor may range from about 1:0.1 to about 1:5.

(iii) Solvent

In some embodiments, the reaction mixture may further comprise a solvent. Suitable solvents and ratios of solvent to the starting substrate are listed above in section (II)(a)(ii). In exemplary embodiments, the solvent may be tetrahydrofuran, and the volume to mass ratio of the solvent to the compound comprising Formula (I) may range from about 2:1 to about 20:1.

(b) Reaction Conditions

In general, the reaction is conducted at a temperature that ranges from about 10° C. to about 80° C. In various embodiments, the reaction may be conducted at a temperature from about 10° C. to about 20° C., from about 20° C. to about 30° C., from about 30° C. to about 50° C., or from about 50° C. to about 80° C. In exemplary embodiments, the temperature of the reaction may range from about 20° C. to about 30° C. The reaction generally is performed under ambient pressure.

Typically, the reaction is allowed to proceed for a sufficient period of time until the reaction is complete, as detailed above. In a completed reaction, the amount of the compound comprising Formula (I) remaining in the reaction mixture may be less than about 3%, or less than about 1%. In general, the reaction may proceed for about 2 hours to about 24 hours. In some embodiments, the reaction may proceed for about 2 hours to about 6 hours, from about 6 hours to about 12 hours, or from about 12 hours to about 24 hours.

The compound comprising Formula (II) may be isolated from the reaction mixture using techniques known to those of skill in the art. Non-limiting examples of suitable techniques include precipitation, extraction, evaporation, distillation, chromatography, and crystallization.

In general, the yield of the compound comprising Formula (II) will be at least about 40% by weight. In certain embodiments, the yield of the compound comprising Formula (II) may be at least about 60%, at least about 70%, at least about 80%, at least about 90%, or at least about 95%.

C-14 in the compounds comprising Formulas (I) and (II) may have an R or an S configuration.

(IV) Methods of Using Compounds Comprising Formula (V)

Yet another aspect of the present disclosure provides methods of using the compounds comprising Formula (V).

(a) Inhibiting Cancer Cell Growth

In one embodiment, a compound comprising Formula (V) or a pharmaceutically acceptable salt thereof may be used to inhibit cancer cell growth, wherein the method comprises contacting a cancer cell with an effective about of a compound comprising Formula (V):

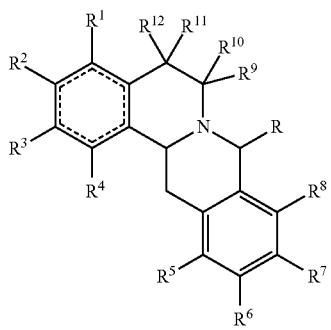

(V)

wherein:
R is hydrogen, hydrocarbyl, or substituted hydrocarbyl;
$R^1$ $R^2$, $R^3$, and $R^4$ independently are hydrogen, halogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising $\{-\}O(CH_2)_nO\{-\}$;
$R^5$, $R^6$, $R^7$, and $R^8$ independently are hydrogen, halogen, $OR^{15}$, $NR^{15}N$ nitro, cyano, thiol, hydrocarbyl, substituted hydrocarbyl, or together $R^6$ and $R^7$ along with the ring carbons to which they are attached form a ring comprising $\{-\}O(CH_2)_nO\{-\}$;
$R^9$, $R^{10}$, $R^{11}$, $R^{12}$, $R^{15}$, and $R^{16}$ independently are hydrogen, hydrocarbyl, or substituted hydrocarbyl;
n is an integer from 1 to 3; and
the dashed lines represent optional double bonds.

In some embodiments, R may be hydrogen, alkyl, heterocylic, aryl, heteroaryl, substituted alkyl, substituted heterocyclic, substituted aryl, or substituted heteroaryl. In various iterations, R may be lower alkyl, which is defined herein as $C_1$-$C_6$, and may be linear or cyclic. In other iterations, R may be morpholinyl, piperizinyl, phenyl, benzyl, pyridyl, pyridazinyl, pyranyl, oxazinyl, piperonyl, etc. Any of the foregoing may be substituted with at least one alkyl, alkenyl, alkynyl, aryl, halogen, oxo, keto, hydroxy, acyl, acyloxy, alkoxy, alkenoxy, alkynoxy, aryloxy, nitro, amino, amine, amide, thiol, cyano, ketal, acetal, ester, or ether.

In various embodiments $R^2$ and $R^3$ independently may be hydrogen, halogen, hydroxy, alkyoxy, alkyl or together $R^2$ and $R^3$ may form $\{-\}O-CH_2-O\{-\}$. In other embodiments, $R^5$ and $R^8$ independently may be hydrogen, halogen, hydroxy, alkoxy, or alkyl. In further embodiments, $R^6$ and $R^7$ independently may be hydrogen, halogen, hydroxy, alkoxy, alkyl, aryloxy, substituted aryloxy, nitro, amino, amine, or amide. In other embodiments, each of $R^9$, $R^{10}$, $R^{11}$, and $R^{12}$ may be hydrogen. In various embodiments, the ring containing the dashed lines may have one, two, or three double bonds. The configuration of each of C-14 and C-8 may be R or S. In exemplary embodiments, C-14 and C-8 have a syn stereochemistry.

In specific embodiments, the compound comprising Formula (V) may be a compound comprising Formula (V-1). In other embodiments, the compound comprising Formula (V) may be a compound comprising Formula (V-1a) or Formula (V-1 b).

The method comprises contacting a cancer cell with an effective amount of the compound comprising Formula (V). An "effective" amount refers to the dose of the compound that affects (i.e., positively or negatively) a process of interest (e.g., cell proliferation or a process involved therein). The precise amount to be used can be determined by the skilled practitioner in view of desired dosages and side effects of the compound.

In some embodiments, the cancer cell may be in vitro. The cancer cell may be a primary cancer cell or a cultured cancer cell line cell. The cancer cell line may be a human cancer cell line or a mammalian cancer cell line. Human or other mammalian cancer cell lines are commercially available and/or are well known to those skilled in the art. The in vitro cancer cell may be contacted with the compound comprising Formula (V) continuously, for a short period of time, intermittently, or any of a variety of regimes.

In other embodiments, the cancer cell may be in vivo, i.e., the cancer cell may be disposed in a subject. In some embodiments, the subject may be a human. In other embodiments, the subject may be a non-human animal. Non-limiting examples of non-human animals include companion animals (e.g., cats, dogs, horses, rabbits, gerbils), agricultural animals (e.g., cows, pigs, sheep, goats, fowl), research animals (e.g., rats, mice, rabbits, primates), and zoo animals (e.g., lions, tiger, elephants, and the like).

The cancer in the subject may be primary or metastatic; the tumor may be malignant or benign. The cancer may be early stage or late stage. Non-limiting examples of cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

In embodiments in which the cancer cell is in vivo, the cancer cell generally is contacted with the compound by administering an effective amount of the compound comprising Formula (V) to the subject. The compound may be administered orally (as a solid or a liquid), parenterally (which includes intramuscular, intravenous, intradermal, intraperitoneal, and subcutaneous), or topically (which includes transmucosal and transdermal). An "effective" amount refers to the dose of the compound that inhibits the growth of the cancer cell. The amount to be used can be determined by the skilled practitioner in view of desired dosages and side effects of the compound. The compound comprising Formula (V) may be administered once or repeatedly to the subject. Repeated administrations may be at regular intervals of 2 hours, 6 hours, 12 hours, 24 hours, 2 days, 5 days, 7 days, 30 days, and so forth.

Following contact with the compound, the growth of the cancer cell generally is inhibited. In some embodiments, cancer cell growth may be inhibited about 0.5-fold, about 1-fold, about 2-fold, about 5-fold, about 10-fold, or more than 10-fold. In other embodiments, cancer cell growth may be inhibited to such a degree that the cell undergoes cell death (via apoptosis or necrosis).

(b) Analgesia

In another embodiment, a compound comprising Formula (V) or a pharmaceutically acceptable salt thereof may be used alone or in combination with at least one additional therapeutic agent for the treatment of a pain condition in a subject. The method comprises administering an effective amount of the compound(s) to a subject. In general, the subject to be treated has been diagnosed as having a pain condition. As used herein, the term "pain" refers to the unpleasant sensory and emotional experience associated with actual or perceived tissue damage by a noxious stimulus. The pain may be acute or chronic pain. For example, the pain may be traumatic or inflammatory pain, which results from injury to non-neural tissue. Non-limiting examples of traumatic or inflammatory pain include arachnoiditis, arthritis, back pain, burn pain, central pain syndrome, cancer pain, headaches (including migraines, cluster, and tension headaches); head and facial pain, muscle pain (including fibromyalgia), myofascial pain syndromes; reflex sympathetic dystrophy syndrome, repetitive stress injuries, sciatica, shingles and other skin disorders, sports injuries, spinal stenosis, surgical pain, temporomandibular disorders, trauma, and/or vascular disease or injury.

Alternatively, the pain may be neuropathic pain, which results from injury to or inflammation of the central or peripheral nervous system. Neuropathic pain may occur in any part of the body and is frequently described as a hot, burning sensation, which can be devastating to the affected individual. Neuropathic pain may be acute or chronic; it may result from diseases that affect nerves (such as diabetes), from trauma, surgical procedures, arthritis, AIDS, burn injuries, cerebral or lumbar spine disease, fibromyalgia, post-ischemic pain, tumors, viral neuralgias, or, because chemotherapy drugs can affect nerves, it may be a consequence of cancer treatment. Among the many neuropathic pain conditions are diabetic neuropathy (which results from nerve damage secondary to vascular problems that occur with diabetes); reflex sympathetic dystrophy syndrome, which may follow injury; phantom limb and post-amputation pain, which may result from the surgical removal of a limb; post-herpetic neuralgia, which may occur after an outbreak of shingles; and complex regional pain syndrome or central pain syndrome, which may result from trauma to the brain or spinal cord.

Characteristic symptoms of neuropathic pain include hyperesthesia (i.e., enhanced sensitivity to a natural stimulus); allodynia (i.e., widespread tenderness or hypersensitivity to tactile stimuli); hyperalgesia (i.e., abnormal sensitivity to pain); spontaneous burning pain; and/or phantom pain (i.e., perception of pain that is non-existent). Hyperesthesia involves an unusual increased or altered sensitivity to sensory stimuli, including for example, acoustic, cerebral, gustatory, muscular, olfactory, onelric, optic, or tactile. As an example, a painful sensation from a normally painless touch stimulus. Allodynia involves an intensified, unpleasant, and painful perception of stimuli triggered by heat or by contact, which is based on a lowering of the pain threshold for these stimuli, including, for example, a non-noxious stimulus to normal skin. Hyperalgesia involves the excessive perception of a variety of stimuli, again based on a lowering of the pain threshold and thus an abnormally increased pain sense, including for example, auditory or muscular stimuli. Phantom pain involves a perception of pain in a limb that is non-existent, such as perceived pain in a limb that has been amputated, i.e. phantom limb syndrome.

The additional therapeutic agent may be an opiate analgesic (e.g., morphine, oxycodone, oxymorphone, hydrocodone, hydromorphone, codeine, etc.) or a nonopiate analgesic (e.g., tramadol, tapentadol, acetaminophen, a non-steroidal anti-inflammatory agent). A person skilled in the art is able to determine an effective amount of the compound to be administered to the subject. In general, the subject may be a human or a non-human mammalian animal (example of which are presented above).

Definitions

The compounds described herein may have asymmetric or chiral centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denotes optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are simply intended to further illustrate and explain the present invention. The invention, therefore, should not be limited to any of the details in these examples.

Example 1

Preparation of Compound 7 Methylamide from Compound 7

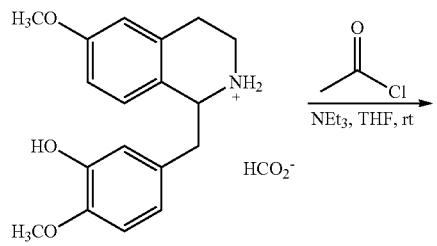

Chemical Formula: C₁₉H₂₃NO₅
Exact Mass: 345.16
Molecular Weight: 345.39
Cmpd 7

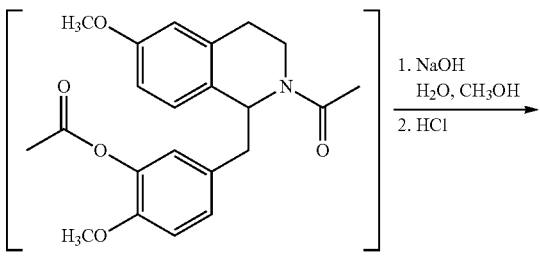

Chemical Formula: C₂₂H₂₅NO₅
Exact Mass: 383.17
Molecular Weight: 383.44

1. NaOH H₂O, CH₃OH
2. HCl

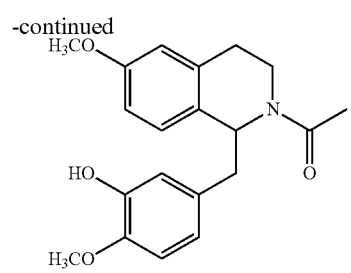

Chemical Formula: C₂₀H₂₃NO₄
Exact Mass: 341.16
Molecular Weight: 341.40
Cmpd 7 methylamide Compound 7 (20.01 g, 0.06 moles) was dissolved in anhydrous tetrahydrofuran (100 mL). To this solution was added triethylamine (17.59 g, 0.17 moles, 24.22 mL) dropwise. Using an addition funnel, acetyl chloride (9.10 g, 0.12 moles, 8.24 mL) was added dropwise. Then, the reaction was stirred at room temperature for 4 hours. Distilled water (10 mL) was added and the entire mixture was evaporated to thick oil under reduced pressure. Added methanol (50 mL) and distilled water (10 mL). To this solution was added 50% aqueous sodium hydroxide (1 mL) to pH 13.0. The mixture was stirred overnight at room temperature. The pH of the solution was adjusted to pH 5.0 using a dropwise addition of 36% hydrochloric acid. The mixture was extracted using ethyl acetate (2×100 mL). The extracts were combined, washed with distilled water (3×100 mL), dried over anhydrous magnesium sulfate, and then filtered. Upon standing, a precipitation began to form from the ethyl acetate solution. The precipitate was isolated by filtration and dried on the funnel producing the methylamide of compound 7 (17.60 g, 89% yield).

Example 2

Preparation of Methyl-Berbine from Compound 7 Methylamide

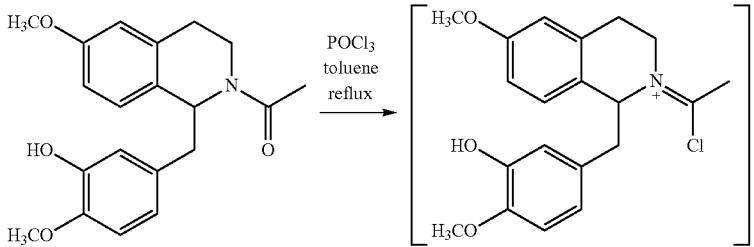

Chemical Formula: C₂₀H₂₃NO₄
Exact Mass: 341.16
Molecular Weight: 341.41

POCl₃
toluene
reflux

Chemical Formula: C₂₀H₂₃ClNO₃⁺
Exact Mass: 360.14
Molecular Weight: 360.86

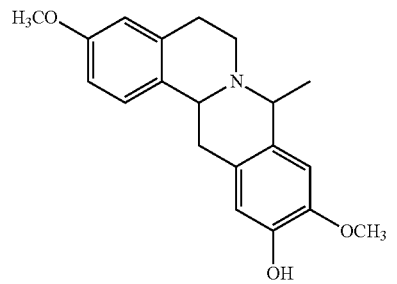

Chemical Formula: C₂₀H₂₃NO₃
Exact Mass: 325.17
Molecular Weight: 325.41
Berbine

NaBH₄
CH₃OH, H₂O

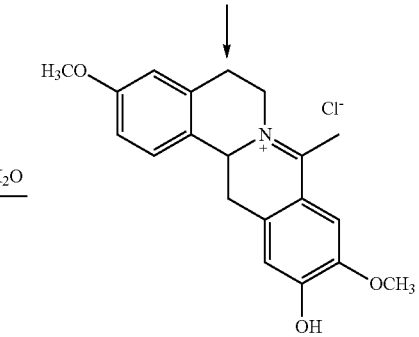

Chemical Formula: C₂₀H₂₂ClNO₃
Exact Mass: 359.13
Molecular Weight: 359.85

Compound 7 methylamide (3.50 g, 0.01 moles) was slurried in toluene (50 mL). The slurry was warmed to 70° C., then cooled to 50° C. To the cooled solution was added phosphorus oxychloride (1.96 g, 0.01 moles, 1.19 mL). The mixture was warmed to reflux and held at reflux 5 hours, then cooled to room temperature. An orange precipitate formed. The toluene was decanted and methanol (100 mL) was added. The mixture was evaporated to thick oil. To this thick oil was added methanol (20 mL), distilled water (10 mL), then sodium borohydride (780 mg, 0.02 moles). The reaction was stirred for 30 minutes at room temperature. The mixture was poured into chloroform (100 mL), then distilled water (50 mL) and 1% aqueous hydrochloric acid (1 mL) were added. The chloroform layer was removed and the remaining aqueous layer was discarded. The chloroform layer was dried over anhydrous magnesium sulfate (2.0 g), filtered, and evaporated to dryness to thick oil. The oil was dissolved in ethyl acetate (10 mL) and was allowed to stand at room temperature. Upon standing, a precipitate formed. The berbine 1 (2.40 g, 72% yield) was isolated by filtration and washing the precipitate with ethyl acetate (1 mL).

Example 3

Preparation of Compound (R)-7 N-Formate

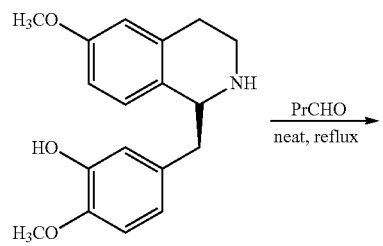

Chemical Formula: C$_{18}$H$_{21}$NO$_3$
Exact Mass: 299.15
Molecular Weight: 299.36
(R)-7

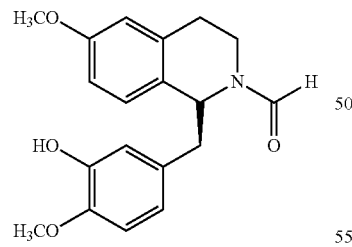

Chemical Formula: C$_{19}$H$_{21}$NO$_4$
Exact Mass: 327.15
Molecular Weight: 327.37
(R)-7 CHO Compound (R)-7 (4.85 g, 16.20 mmol) was slurried in 30 mL propyl formate. This mixture was warmed to reflux and maintained at reflux for 12 hours. The reaction was cooled to room temperature then evaporated under reduced pressure to an oil. To the crude oil, ethyl acetate (10 mL) was added and the solution was evaporated once again to form a foam. This foam was dried overnight at room temperature yielding the N-formyl compound (5.30 g, 16.2 mmol, 100% yield) as a mixture of rotamers.

Example 4

Preparation of Berbine from Compound (R)-7 N-Formate

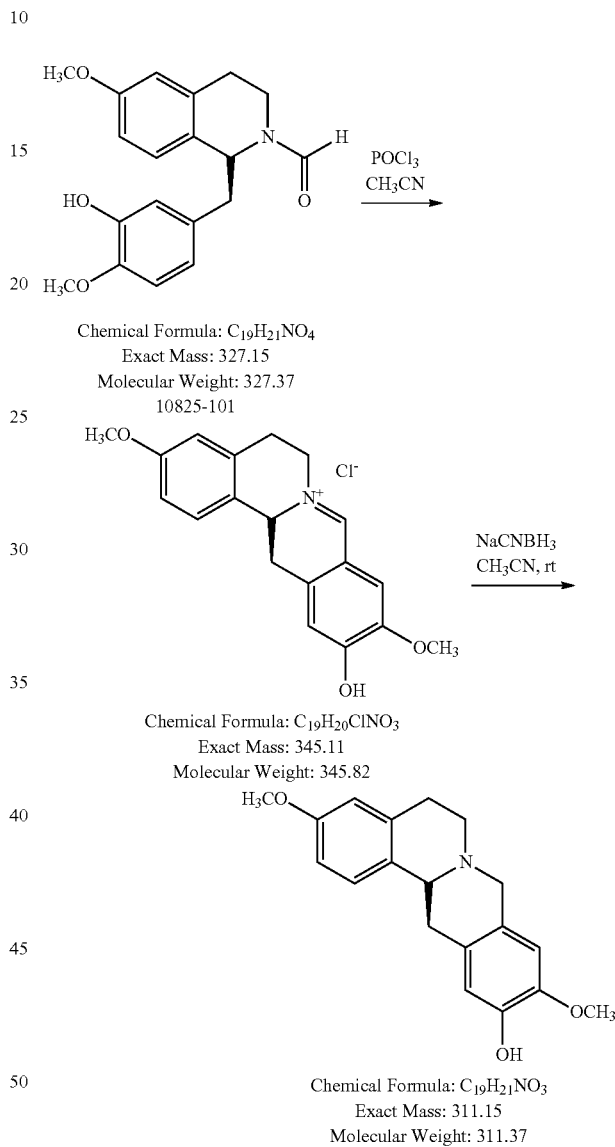

Into a 3 neck round bottom flask was charged N-formyl (R)-7 (1.2 2 g, 3.73 mmol) and acetonitrile (15 mL). To this solution was added phosphorus oxychloride (2.0 eq., 7.45 mmol, 1.14 g, 0.69 mL) dropwise. After the addition was complete, the mixture was stirred at room temperature overnight. At that time, the solvent was removed under vacuum to form an orange oil. The oil was redissolved in acetonitrile (20 mL) then sodium cyanoborohydride (2.0 eq., 7.45 mmol, 0.47 g) was added. This mixture was stirred at room temperature for 1 hour at which time the reaction was deemed complete. Distilled water (20 mL) was added and this mixture was stirred for 1 hour. Extraction of this reaction mixture was accomplished using ethyl acetate (3×20 mL). The extracts were combined, dried over anhydrous sodium sulfate, filtered, and then evaporated. The product berbine (1.0 g, 3.21 mmol, 85% yield) was isolated using column chromatography (SiO$_2$ G60, 70 to 230 mesh) eluting with a gradient from 0% EtOAc/hexanes to 50% EtOAc/hexanes, combining similar fractions by TLC, evaporating to a foam, and then drying the foam under vacuum at room temperature for 48 hours.

Example 5

Preparation of Compound (R)-7 Propylamide

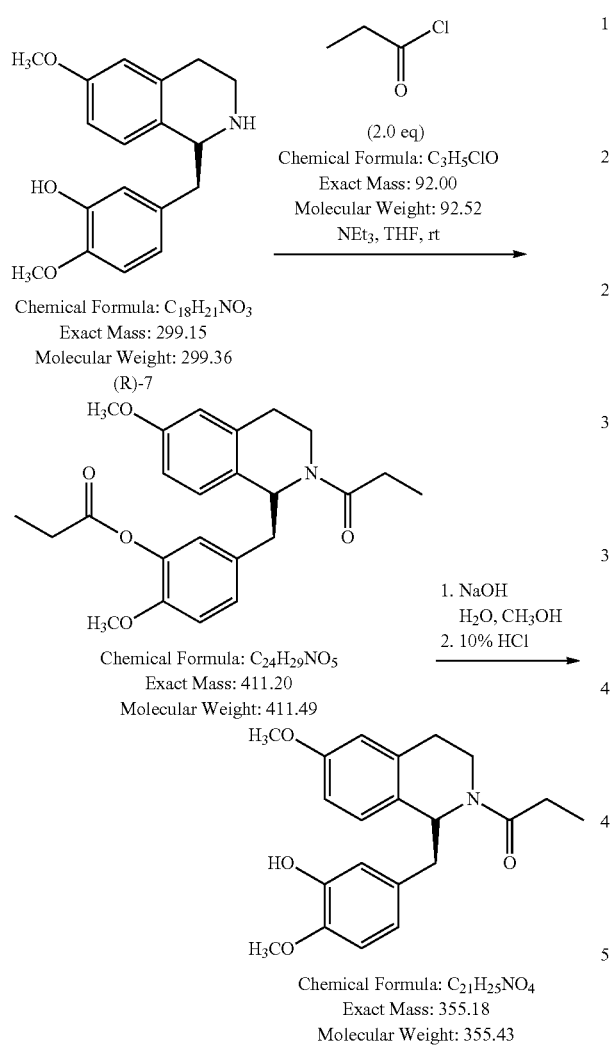

ture for 16 hours, the pH was adjusted to 5.0 using 10% HCl/H$_2$O, and then an additional 25 mL of distilled water was added. The solution was extracted using EtOAc (3×25 mL), the extracts were combined, dried over anhydrous Na$_2$SO$_4$, filtered, and then concentrated to an oil. The oil was placed in vacuum at room temperature for 48 hours where the material solidified producing the N-propyl amide (14.23 g, 40.03 mmol, 97% yield).

Example 6

Preparation of Ethyl-Berbine from Compound (R)-7 Propylamide

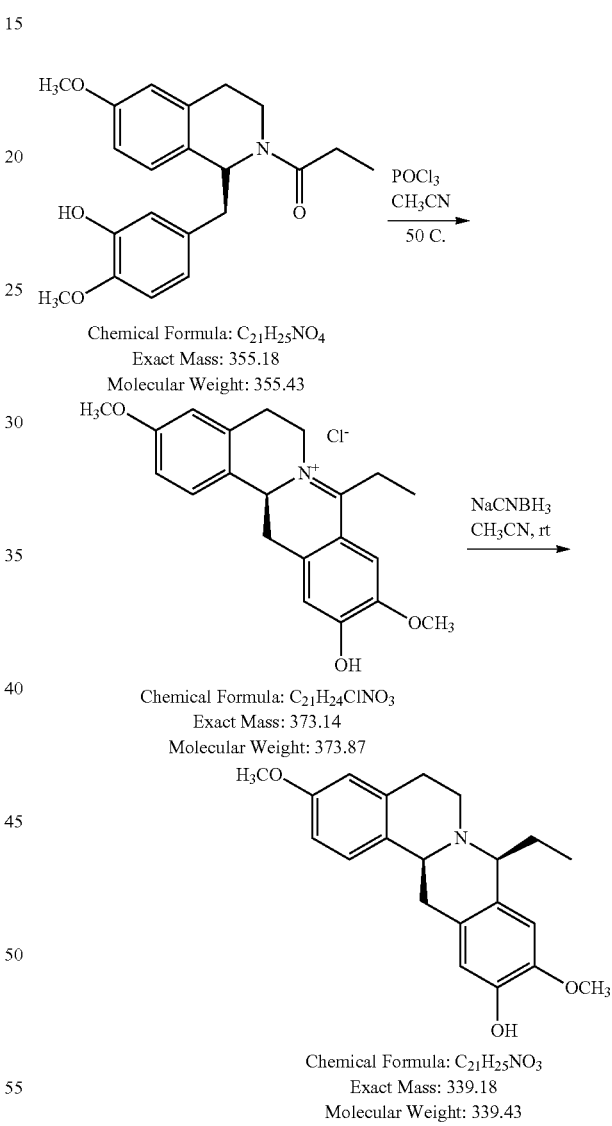

Into a round bottom flask was charge (R)-7 (12.36 g, 41.29 mmol) and tetrahydrofuran (100 mL). To this slurry was added triethylamine (2.10 eq., 86.71 mmol, 8.77 g, 12.1 mL) and propionyl chloride (2.05 eq., 84.64 mmol, 7.83 g, 7.4 mL) dropwise. The reaction was stirred at room temperature for 16 hours, after which the reaction was deemed complete. The reaction mixture was filtered through a fritted funnel, and the solid was washed with EtOAc (50 mL). The filtrate was transferred to a round bottom flask and evaporated to an oil. To the oil was added methanol (25.0 mL) and distilled water (10.0 mL). To this solution was added solid sodium hydroxide (2.0 eq., 82.58 mmol, 3.30 g). After stirring at room tempera- Into a 3 neck round bottom flask was charged (R)-7 N-propylamide (1.54 g, 4.33 mmol) and acetonitrile (15 mL). To this solution was added phosphorus oxychloride (1.0 eq., 4.33 mmol, 0.66 g, 0.40 mL) dropwise. After the addition was complete, the mixture was warmed to 50° C. and stirred for 12 hours, then cooled to room temperature and stirred for 4 hours. At that time, sodium cyanoborohydride (1.0 eq., 4.33 mmol, 0.27 g) was added. This mixture was stirred at room temperature for 6 hours, at which time the reaction was deemed complete. Distilled water (30 mL) was added and the pH was adjusted to 1.0 using 10% HCl/H₂O. This reaction mixture was stirred at room temperature for 24 hours. After adjusting the pH to 9.2 using 29% NH₃/H₂O, the reaction was extracted using ethyl acetate (3×25 mL). The extracts were combined, dried over anhydrous sodium sulfate, filtered, and then evaporated. The product berbine (1.3 g, 3.83 mmol, 88% yield) was isolated using column chromatography (SiO₂ G60, 70 to 230 mesh) eluting with a gradient from 0% EtOAc/hexanes to 50% EtOAc/hexanes, combining similar fractions by TLC, evaporating to a foam, and then drying the foam under vacuum at room temperature for 48 hours.

Example 7

Preparation of Compound (R)-7 Benzamide

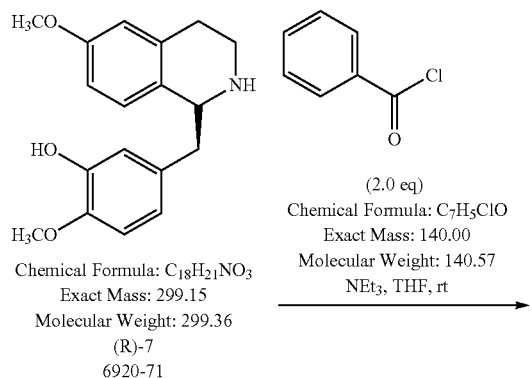

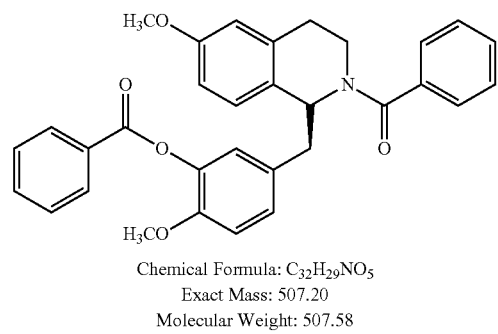

Into a round bottom flask was charge (R)-7 (1.92 g, 6.41 mmol) and tetrahydrofuran (15 mL). To this slurry was added triethylamine (2.10 eq., 13.46 mmol, 1.31 g, 1.88 mL) and then benzoyl chloride (2.05 eq., 13.15 mmol, 1.84 g, 1.53 mL) dropwise. The reaction was stirred at room temperature for 16 hours, at which time the reaction was deemed complete. To the reaction was added distilled water (25.0 mL) and then extracted using EtOAc (3×25 mL), the extracts were combined, and evaporated to an oil. To the oil was added methanol (10.0 mL) and distilled water (5.0 mL). To this solution was added 50% NaOH/H₂O (5.0 mL). After stirring at room temperature for 16 hours, the pH was adjusted to 5.0 using 10% HCl/H₂O, and then an additional 25 mL of distilled water was added. The solution was extracted using EtOAc (3×25 mL), the extracts were combined, dried over anhydrous Na₂SO₄, filtered, and then concentrated to an oil. Isolation of the product was accomplished through column chromatography (SiO₂ G60, 70 to 230 mesh) using gradient elution from 0% EtOAc/hexanes to 60% EtOAc/hexanes. Similar fractions monitored by TLC were combined, evaporated to a foam, and placed under vacuum for 18 hours at room temperature yielding the product (1.88 g, 4.66 mmol, 73% yield) as an off white solid.

Example 8

Preparation of Phenyl-Berbine from Compound (R)-7 Benzamide

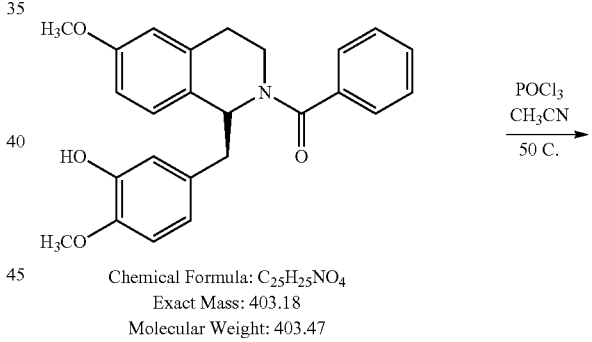

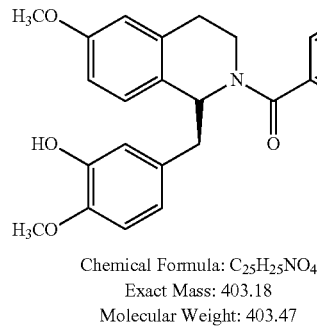

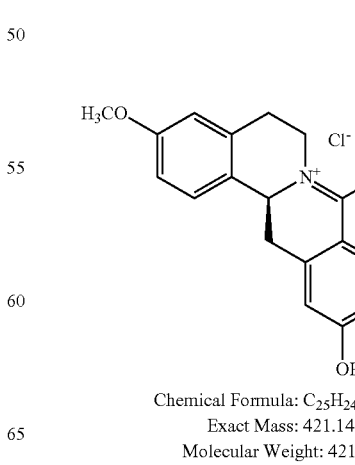

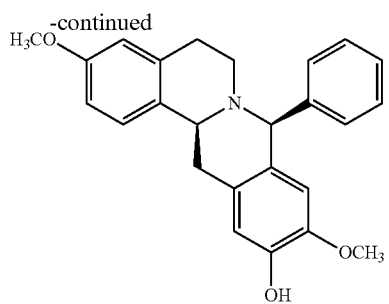

Chemical Formula: C$_{25}$H$_{25}$NO$_3$
Exact Mass: 387.18
Molecular Weight: 387.47

Into a 3 neck round bottom flask was charged (R)-7 N-benzamide (1.84 g, 4.56 mmol) and acetonitrile (25 mL). The reaction was distilled until a vapor temperature of 82° C. was reached, then the solution was cooled to room temperature. To this solution was added phosphorus oxychloride (1.0 eq., 4.56 mmol, 0.70 g, 0.43 mL) dropwise. After the addition was complete, the mixture was warmed to 50° C. and stirred for 20 hours, then cooled to room temperature. At that time, sodium cyanoborohydride (1.0 eq., 4.56 mmol, 0.30 g) was added. This mixture was stirred at room temperature for 18 hours. Distilled water (15 mL) was added and the pH was adjusted to 1.0 using concentrated HCl. This mixture was stirred at room temperature for 24 hour, and then evaporated to ~½ volume. After adjusting the pH to 9.2 using 29% NH$_3$/H$_2$O, the reaction was extracted of using chloroform (3×25 mL). The extracts were combined, dried over anhydrous sodium sulfate, filtered, and then evaporated. The product berbine (0.86 g, 2.22 mmol, 49% yield) and (R)-7 N-benzamide (0.84 g) was isolated using column chromatography (SiO$_2$ G60, 70 to 230 mesh) eluting with a gradient from 0% EtOAc/hexanes to 25% EtOAc/hexanes, combining similar fractions by TLC, evaporation to a foam, and then drying the foam under vacuum at room temperature for 48 hours. Based on recovery of the (R)-7 N-benzamide, the yield of the reaction was 89%.

The present invention is not limited to the above embodiments and may be variously modified. The above description of exemplary embodiments is intended only to acquaint others skilled in the art with the invention, its principles and its practical application so that others skilled in the art may adapt and apply the invention in its numerous forms, as may be best suited to the requirements of a particular use.

Example 9

Preparation of Berbine Derivative from Compound Br—(R)-7

Different regioisomers of berbine can be prepared by including a halogen group in the starting compound, such that cyclization is directed to the least hindered position. The reaction scheme below demonstrates this approach.

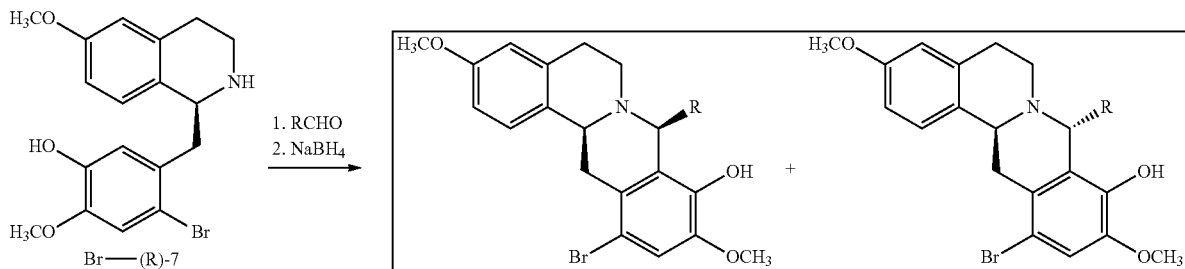

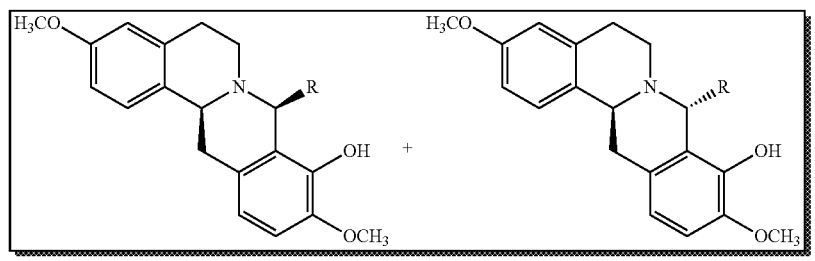

Reaction with RCHO (step 1) can be performed as detailed above in Examples 1, 3, 5, and 7, and the cyclization and reduction step (2) can be performed as described above in Examples 2, 4, 6, and 8. The halogen group can be removed by contact with 10% PD/C, formic acid, and triethylamine in isopropyl alcohol at reflux.

Example 10

Preparation of Substituted Phenyl-Berbine

Substituted aromatic derivatives of berbine can be prepared according to the following scheme. X can be halogen, $NO_2$, $CH_3$, or $OCH_3$.

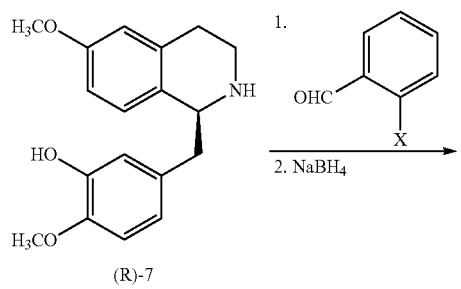

(R)-7

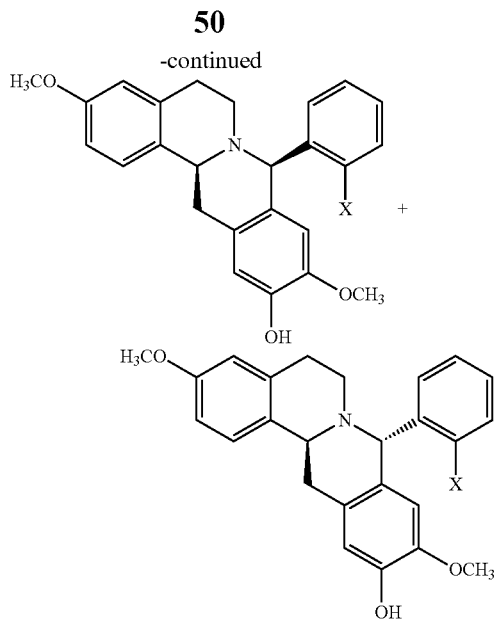

Example 11

Preparation of Ether or Amine Derivatives of Phenyl-Berbine

Ether and amine derivatives of phenyl berbine can be prepared according to the following scheme.

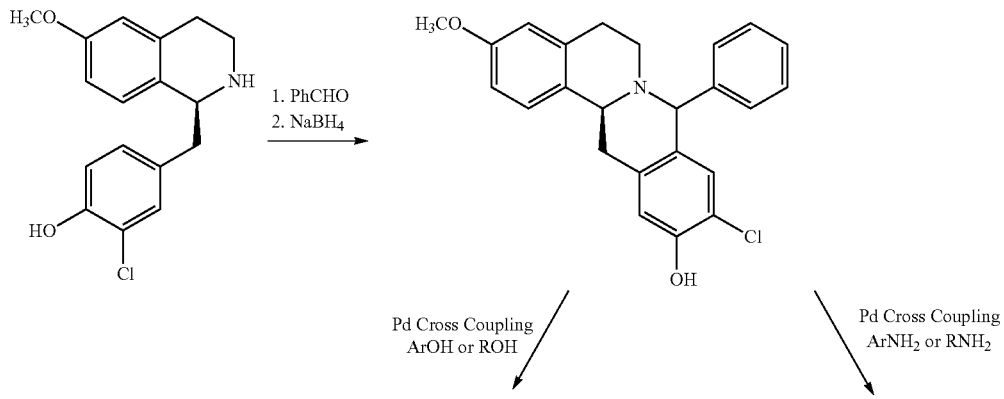

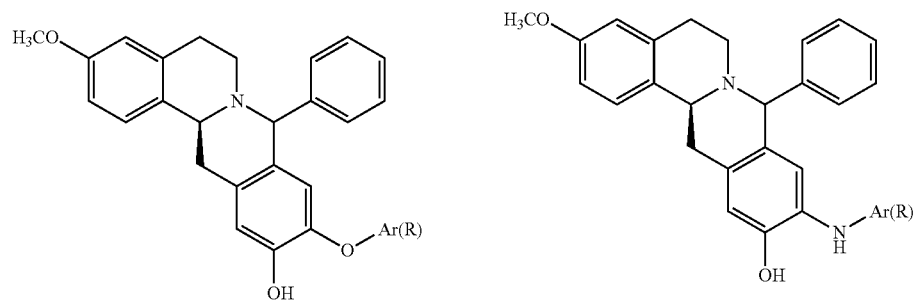

Step 1 can be performed as detailed above in Examples 1, 3, 5, and 7, and step 2 can be performed as described above in Examples 2, 4, 6, and 8. The product can be contacted with (1-5 eq.) of alcohol or amine, (0.01-1%) transition metal catalyst, and (1-4 eq.) sodium tert-butoxide, potassium carbonate, or triethylamine. The reaction can be conducted in the presence of toluene, THF, DMF, or DMAC, and at a temperature ranging from room temperature to reflux.

Example 12

Preparation of Amide Derivatives of Phenyl-Berbine

Amide derivatives of phenyl berbine can be prepared according to the following scheme.

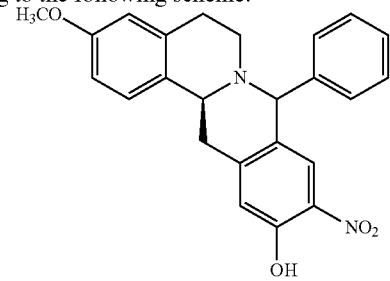
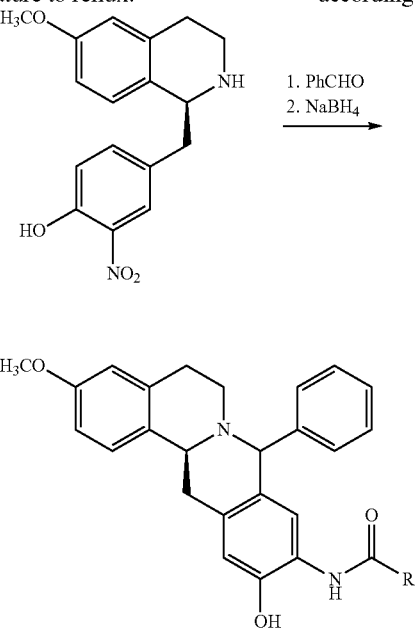

Step 1 can be performed as detailed above in Examples 1, 3, 5, and 7, and step 2 can be performed as described above in Examples 2, 4, 6, and 8. Reduction of $NO_2$ to $NH_2$ can be carried out in the presence of hydrogen and a transition metal catalyst. The amide can be formed by contact with (1.0-1.2 eq.) acyl halide and (1-4 eq.) triethylamine, diisopropylethylamine, or N-methyl morpholine. Reaction with the acyl halide can be conducted in the presence of THF, acetonitrile, dichloromethane, or chloroform and the reaction can be conducted at room temperature.

Example 13

B16 Cancer Cell Screening Assay

The murine melanoma cell line, B16, was used to screen the activity of compounds comprising Formula (V). B16 cells were grown under standard conditions and exposed to several concentrations of each of the tested compounds. Table 1 shows the effects of the tested compounds on the inhibition of B16 proliferation and the inhibition of lactate dehydrogenase (LDH) release.

TABLE 1

| B16 Cancer Cell Screening Data. | | | |
| --- | --- | --- | --- |
| Compound ID | Structure | B16 Profile IC50 | B16 LDH IC50 |
| M-R-0001 | | >600 µM | 175 µM |

TABLE 1-continued

B16 Cancer Cell Screening Data.

| Compound ID | Structure | B16 Profile IC50 | B16 LDH IC50 |
|---|---|---|---|
| M-R-0002 | 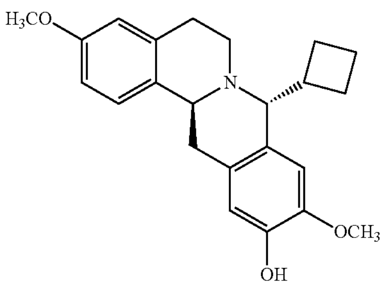 [SMILES: COc1ccc2c(c1)CCN1[C@H]2Cc2cc(O)c(OC)cc2[C@H]1C1CCC1] | 200 μM | 200 μM |
| M-R-0003 | 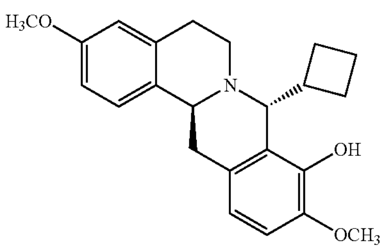 [SMILES: COc1ccc2c(c1)CCN1[C@H]2Cc2ccc(OC)c(O)c2[C@H]1C1CCC1] | >600 μM | 150 μM |
| M-R-0004 | 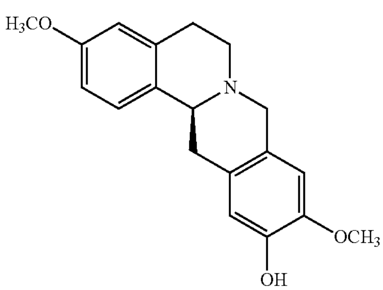 [SMILES: COc1ccc2c(c1)CCN1Cc3cc(OC)c(O)cc3C[C@@H]21] | >600 μM | >600 μM |
| M-R-0005 | 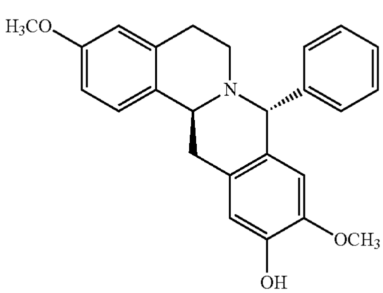 [SMILES: COc1ccc2c(c1)CCN1[C@H](c3ccccc3)c3cc(OC)c(O)cc3C[C@@H]21] | 35 μM | 30 μM |
| M-R-0006 | 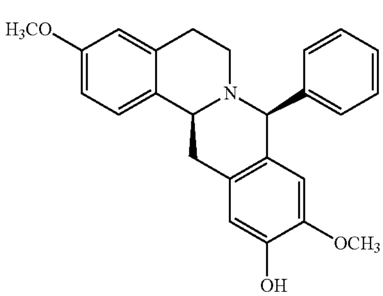 [SMILES: COc1ccc2c(c1)CCN1[C@@H](c3ccccc3)c3cc(OC)c(O)cc3C[C@@H]21] | 35 μM | 35 μM |

TABLE 1-continued

B16 Cancer Cell Screening Data.

| Compound ID | Structure | B16 Profile IC50 | B16 LDH IC50 |
|---|---|---|---|
| M-R-0007 | 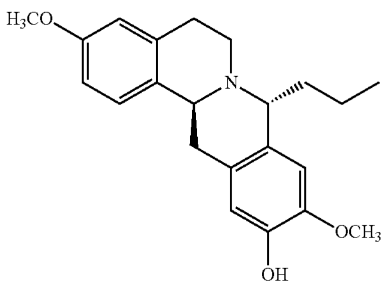 [SMILES: CCC[C@@H]1c2cc(OC)c(O)cc2C[C@H]2c3ccc(OC)cc3CCN12] | >400 μM | Inactive |
| M-R-0008 | 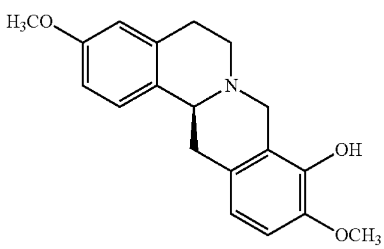 [SMILES: COc1ccc2c(c1)CCN1Cc3c(ccc(OC)c3O)C[C@@H]21] | 38 μM | >320 μM |
| M-R-0009 | 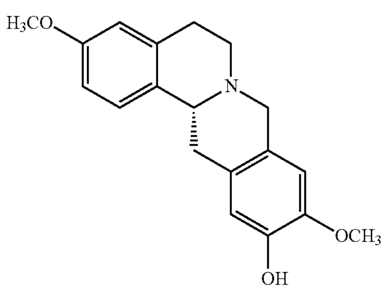 [SMILES: COc1ccc2c(c1)CCN1Cc3cc(OC)c(O)cc3C[C@H]21] | Inactive | Inactive |
| M-R-0010 | 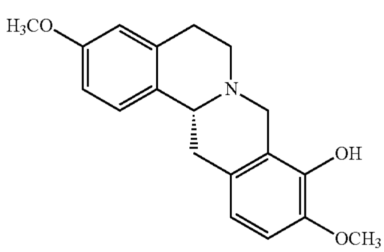 [SMILES: COc1ccc2c(c1)CCN1Cc3c(ccc(OC)c3O)C[C@H]21] | 300 μM | Inactive |
| M-R-0011 | 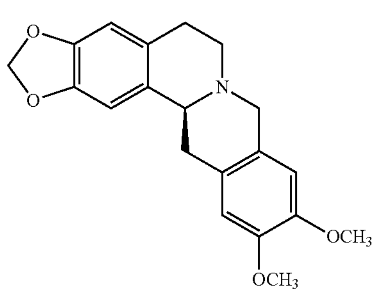 [SMILES: COc1cc2c(cc1OC)CN1CCc3cc4c(cc3[C@@H]1C2)OCO4] | 120 μM | 70 μM |

TABLE 1-continued

B16 Cancer Cell Screening Data.

| Compound ID | Structure | B16 Profile IC50 | B16 LDH IC50 |
| --- | --- | --- | --- |
| M-R-0012 | 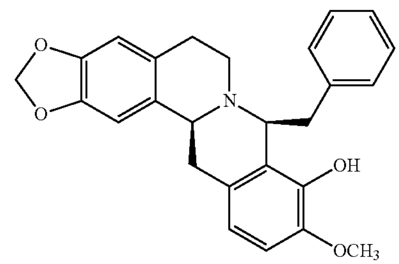 [SMILES: COc1ccc2c(c1O)[C@H](Cc1ccccc1)N1CCc3cc4c(cc3[C@@H]1C2)OCO4] | >600 μM | >700 μM |
| M-R-0013 | 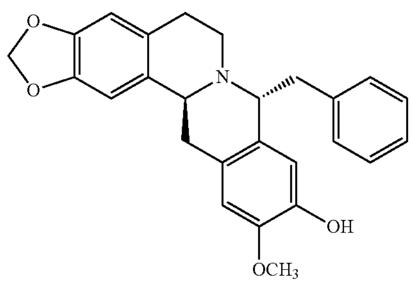 [SMILES: COc1cc2c(cc1O)[C@@H](Cc1ccccc1)N1CCc3cc4c(cc3[C@@H]1C2)OCO4] | 75 μM | 700 μM |
| M-R-0014 | 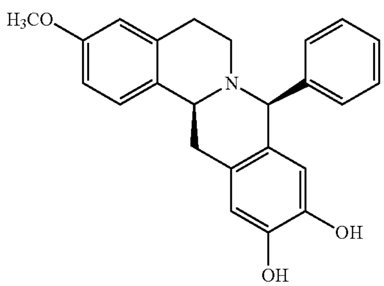 [SMILES: COc1ccc2c(c1)CCN1[C@@H](c3ccccc3)c3cc(O)c(O)cc3C[C@@H]21] | 10 μM | 70 μM |
| M-R-0015 | 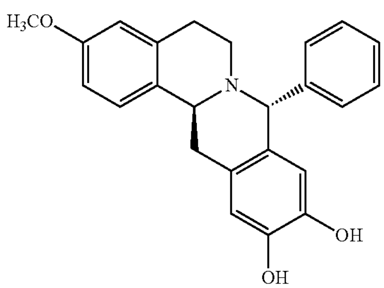 [SMILES: COc1ccc2c(c1)CCN1[C@H](c3ccccc3)c3cc(O)c(O)cc3C[C@@H]21] | 25 μM | 130 μM |
| M-R-0016 | 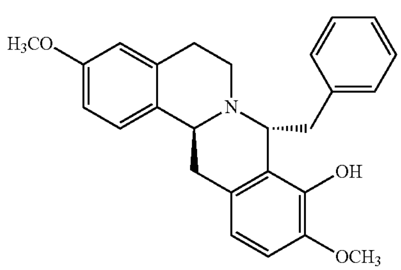 [SMILES: COc1ccc2c(c1)CCN1[C@H](Cc3ccccc3)c3c(ccc(OC)c3O)C[C@@H]21] | 75 μM | 700 μM |

TABLE 1-continued

B16 Cancer Cell Screening Data.

| Compound ID | Structure | B16 Profile IC50 | B16 LDH IC50 |
|---|---|---|---|
| M-R-0017 | 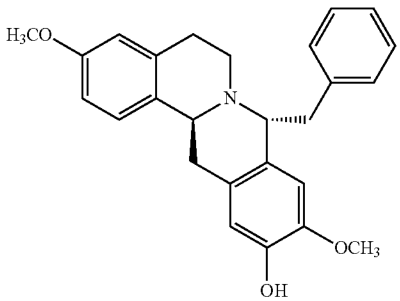 [SMILES: COc1ccc2c(c1)CCN1[C@H](Cc3ccccc3)c3cc(OC)c(O)cc3C[C@@H]21] | 55 μM | 60 μM |
| M-R-0018 | 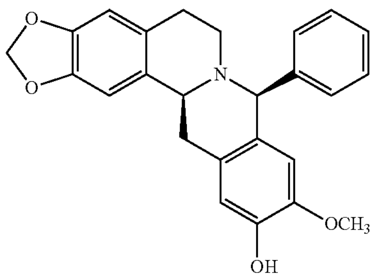 [SMILES: COc1cc2c(cc1O)C[C@H]1c3cc4c(cc3CCN1[C@H]2c1ccccc1)OCO4] | 35 μM | 30 μM |
| M-R-0019 | 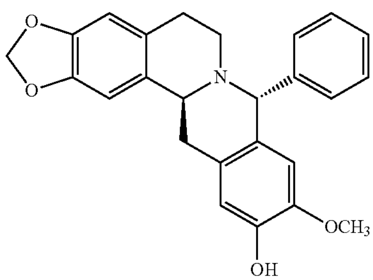 [SMILES: COc1cc2c(cc1O)C[C@H]1c3cc4c(cc3CCN1[C@@H]2c1ccccc1)OCO4] | 45 μM | 50 μM |
| M-R-0020 | 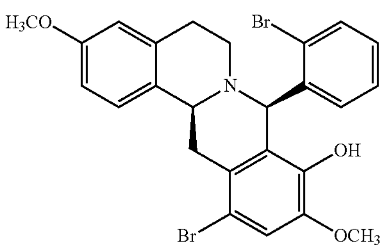 | 18 μM | 30 μM |
| M-R-0021 | 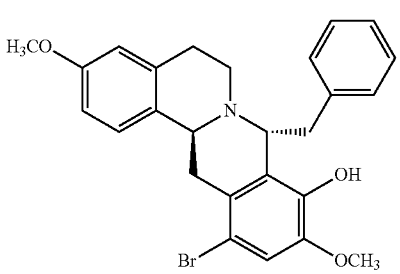 [SMILES: COc1ccc2c(c1)CCN1[C@H](Cc3ccccc3)c3c(O)c(OC)cc(Br)c3C[C@@H]21] | 65 μM | ~350 μM |

TABLE 1-continued

B16 Cancer Cell Screening Data.

| Compound ID | Structure | B16 Profile IC50 | B16 LDH IC50 |
|---|---|---|---|
| M-R-0022 | 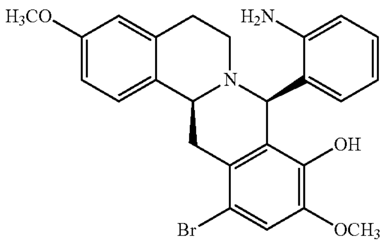 [SMILES: COc1ccc2c(c1)CCN1[C@@H](c3ccccc3N)c3c(O)c(OC)cc(Br)c3C[C@@H]21] | 25 μM | 30 μM |
| M-R-0023 | 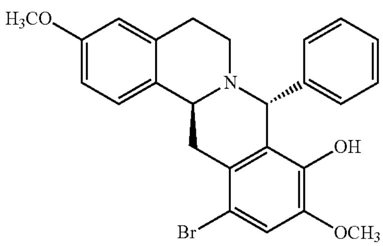 [SMILES: COc1ccc2c(c1)CCN1[C@H](c3ccccc3)c3c(O)c(OC)cc(Br)c3C[C@@H]21] | 27 μM | 40 μM |
| M-R-0024 | 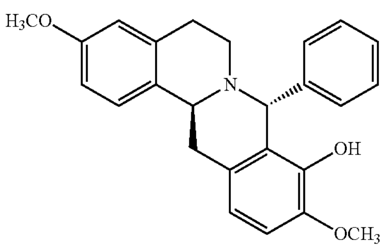 [SMILES: COc1ccc2c(c1)CCN1[C@H](c3ccccc3)c3c(ccc(OC)c3O)C[C@@H]21] | 60 μM | 70 μM |
| M-R-0025 | 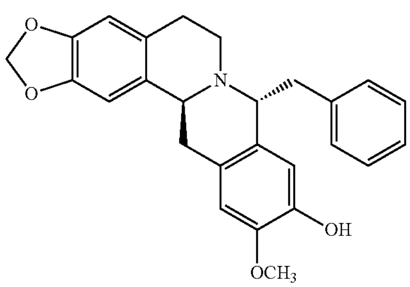 [SMILES: COc1cc2c(cc1O)[C@@H](Cc1ccccc1)N1CCc3cc4c(cc3[C@@H]1C2)OCO4] | >160 μM | ~350 μM |
| M-R-0026 | 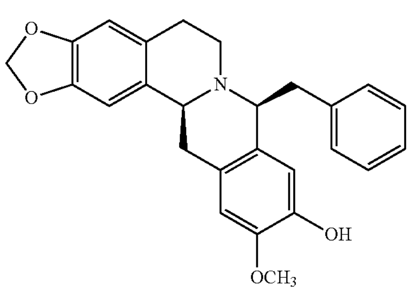 [SMILES: COc1cc2c(cc1O)[C@H](Cc1ccccc1)N1CCc3cc4c(cc3[C@@H]1C2)OCO4] | 55 μM | 60 μM |

What is claimed is:

1. A compound of Formula (V-1):

(V-1)

[Structure shown]

wherein:
- $R^1$ $R^2$, $R^3$, and $R^4$ independently are hydrogen, halogen, $OR^{15}$, $NR^{15}N^{16}$, nitro, cyano, thiol, hydrocarbyl, substituted hydrocarbyl, or together $R^2$ and $R^3$ along with the ring carbons to which they are attached form a ring comprising $\{-\}O(CH_2)_nO\{-\}$;
- $R^5$, $R^6$, $R^7$, and $R^8$ independently are hydrogen, halogen, $OR^{15}$, $NR^{15}N^{16}$, nitro, cyano, thiol, hydrocarbyl, substituted hydrocarbyl, or together $R^6$ and $R^7$ along with the ring carbons to which they are attached form a ring comprising $\{-\}O(CH_2)_nO\{-\}$; provided that at least two of $R^6$, $R^7$, and $R^8$ are other than methoxy;
- $R^9$, $R^{10}$, $R^{11}$, and $R^{12}$ independently are hydrogen, hydrocarbyl, or substituted hydrocarbyl;
- $R^{21}$, $R^{22}$, $R^{23}$, $R^{24}$, and $R^{25}$ independently are hydrogen, halogen, $OR^{15}$, $NR^{15}N^{16}$, nitro, cyano, thiol, hydrocarbyl, or substituted hydrocarbyl;
- $R^{15}$ and $R^{16}$ independently are hydrogen, hydrocarbyl, or substituted hydrocarbyl;
- m is an integer of 0;
- n is an integer from 1 to 3; and
- the dashed lines represent optional double bonds.

2. The compound of claim 1, wherein each of $R^1$, $R^4$, $R^9$, $R^{10}$, $R^{11}$, and $R^{12}$ is hydrogen; $R^2$ and $R^3$ independently are hydrogen, halogen, hydroxy, alkyoxy, alkyl or together $R^2$ and $R^3$ form $\{-\}O-CH_2-O\{-\}$; $R^5$ and $R^8$ independently are hydrogen, halogen, hydroxy, alkoxy, or alkyl; $R^6$ and $R^7$ independently are hydrogen, halogen, hydroxy, alkoxy, alkyl, aryloxy, substituted aryloxy, nitro, amino, amine, or amide; and $R^{21}$, $R^{22}$, $R^{23}$, $R^{24}$, and $R^{25}$ independently are hydrogen, halogen, hydroxy, alkoxy, alkyl, nitro, amino, or amine.

3. The compound of claim 1, wherein the compound has Formula (V-1a):

(V-1a)

[Structure shown]

wherein:
- $R^2$ is hydroxy or alkyoxy and $R^3$ is hydrogen, or together $R^2$ and $R^3$ form $\{-\}O-CH_2-O\{-\}$;
- $R^5$ and $R^8$ independently are hydrogen, halogen, hydroxy, alkoxy, or alkyl;
- $R^6$ and $R^7$ independently hydrogen, halogen, hydroxy, alkyoxy, alkyl aryloxy, substituted aryloxy, nitro, amino, amine, or amide;
- $R^{20}$ is hydrogen, halogen, hydroxy, alkoxy, alkyl, nitro, amino, or amine; and
- m is 0.

4. The compound of claim 1, wherein the compound has Formula (V-1b):

(V-1b)

[Structure shown]

wherein:
- $R^2$ is hydroxy or alkyoxy and $R^3$ is hydrogen, or together $R^2$ and $R^3$ form $\{-\}O-CH_2-O\{-\}$;
- $R^5$ and $R^8$ independently are hydrogen, halogen, hydroxy, alkoxy, or alkyl;
- $R^6$ and $R^7$ independently hydrogen, halogen, hydroxy, alkyoxy, alkyl arylxoy, substituted aryloxy, nitro, amino, amine, or amide;
- $R^{20}$ is hydrogen, halogen, hydroxy, alkoxy, alkyl, nitro, amino, or amine; and
- m is 0.

5. The compound of claim 1, wherein the compound is chosen from the following compounds:

[Structures shown]

65
-continued
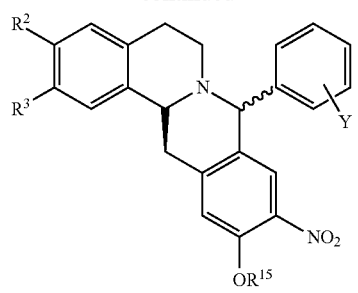
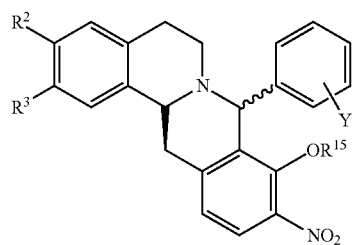
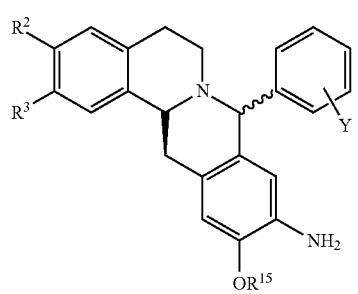
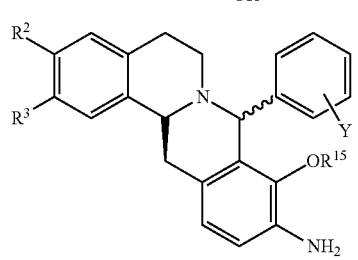
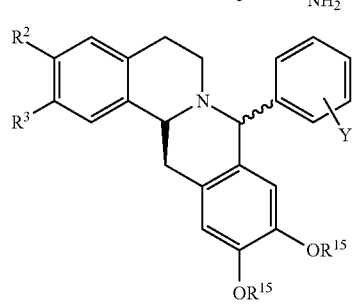
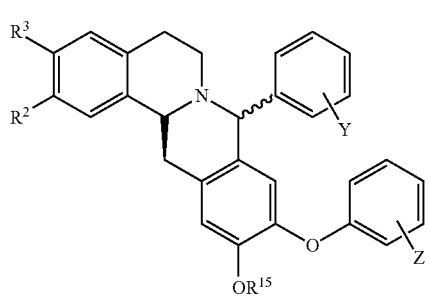
66
-continued
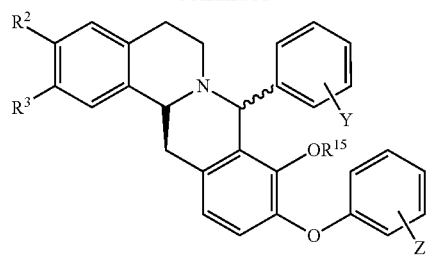
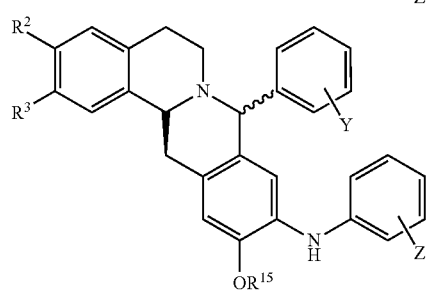
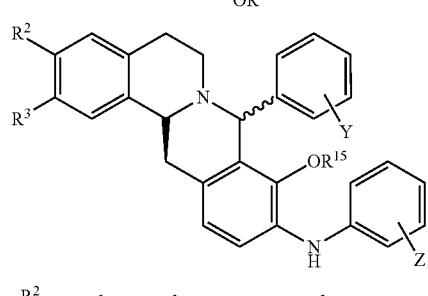
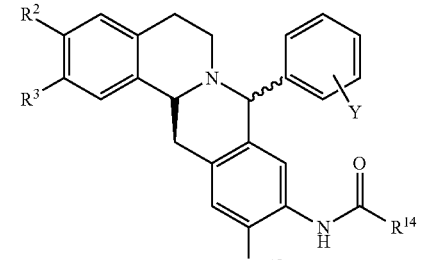
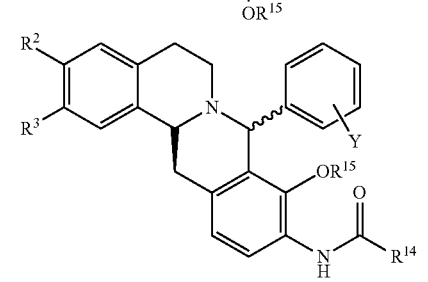
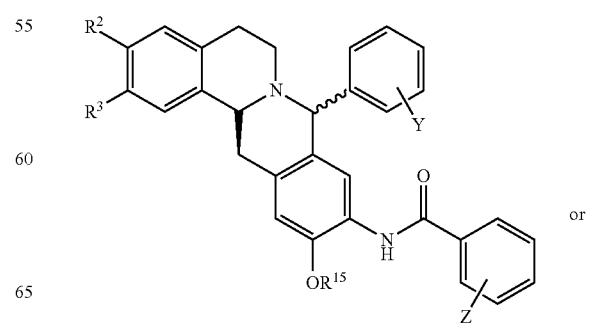
or -continued
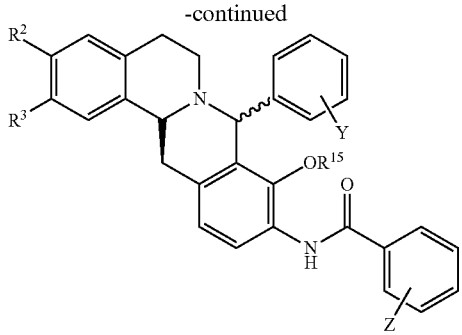
wherein:
R² is hydroxy or alkyoxy and R³ is hydrogen, or together R² and R³ form {—}O—CH$_2$—O{—}
R$^{14}$ is alkyl or substituted alkyl.
R$^{15}$ is hydrogen or C$_1$-C$_6$ alkyl;
X is halogen; and
Y and Z independently are hydrogen, halogen, hydroxy, alkoxy, alkyl, nitro, amino, or amine.
* * * * *